(12) United States Patent
Borden et al.

(10) Patent No.: US 9,545,416 B2
(45) Date of Patent: Jan. 17, 2017

(54) COMBINATION THERAPY USING RIBAVIRIN AS EIF4E INHIBITOR

(75) Inventors: Katherine Borden, Dollard des Ormeaux (CA); Hiba Zahreddine, Montreal (CA); Biljana Culjkovic Kraljacic, Montreal (CA)

(73) Assignee: Universite de Montreal, Montreal, Quebec (CA)

( * ) Notice: Subject to any disclaimer, the term of this patent is extended or adjusted under 35 U.S.C. 154(b) by 147 days.

(21) Appl. No.: 14/344,536

(22) PCT Filed: Sep. 13, 2012

(86) PCT No.: PCT/CA2012/000831
§ 371 (c)(1),
(2), (4) Date: Apr. 3, 2014

(87) PCT Pub. No.: WO2013/037043
PCT Pub. Date: Mar. 21, 2013

(65) Prior Publication Data
US 2014/0343007 A1 Nov. 20, 2014

(30) Foreign Application Priority Data
Sep. 13, 2011 (CA) ..................... 2752008

(51) Int. Cl.
| | | |
|---|---|---|
| *A61K 31/70* | (2006.01) | |
| *A01N 43/04* | (2006.01) | |
| *A61K 31/7068* | (2006.01) | |
| *A61K 31/4402* | (2006.01) | |
| *A61K 31/7056* | (2006.01) | |

(52) U.S. Cl.
CPC ....... *A61K 31/7068* (2013.01); *A61K 31/4402* (2013.01); *A61K 31/7056* (2013.01)

(58) Field of Classification Search
CPC ............ A61K 31/4402; A61K 31/7056; A61K 31/7068; A61K 2300/00
See application file for complete search history.

(56) References Cited

U.S. PATENT DOCUMENTS 7,812,164 B2 * 10/2010 Austad ............... A61K 31/4355
546/115
2009/0181997 A1 7/2009 Grayzel et al.

FOREIGN PATENT DOCUMENTS

WO 2012006584 A2 1/2012
WO 2012019284 A1 2/2012

OTHER PUBLICATIONS

International Search Report dated Mar. 21, 2013, in International Application No. PCT/CA2012/000831 filed on Sep. 13, 2012.
Assouline et al., Blood., 114 (2) pp. 257-260. Epub May 11, 2009, "Molecular Targeting of the Oncogene eIF4E in Acute Myeloid Leukemia (AML): a Proof-of-Principle Clinical Trial With Ribavirin."
Assouline et al., Blood (ASH Annual Meeting Abstracts) 118:Abstract 3606, Dec. 12, 2011, "A Phase I Combination Study of Ribavirin and Low Dose Cytarabine Arabinoside (ara-C) in M4/M5 Acute Myeloid Leukemia (AML) and AML With High eIF4E."
Lobova et al., Eksp. Onkol., 7(3), pp. 63-65. 1985 [Ribamidyl (ribavirin) as a modulator of the biological action of arabinosylcytosine and methotrexate] (Article in Russian).
Kraljacic et al., Leukemia. 25(7), pp. 1197-1200, Epub:1 Apr. 1, 2011. "Inhibition of eIF4E With Ribavirin Cooperates With Common Chemotherapies in Primary Acute Myeloid Leukemia Specimens."
Borden et al., Leuk Lymphoma, 51(10), pp. 1805-1815, Oct. 2010, "Ribavirin as an Anti-Cancer Therapy: Acute Myeloid Leukemia and Beyond?."

* cited by examiner

*Primary Examiner* — Lawrence E Crane
(74) *Attorney, Agent, or Firm* — Downs Rachlin Martin PLLC

(57) ABSTRACT

The present invention relates to pharmaceutical compositions and combination therapies for treating patients having a neoplasm or a proliferative disorder, the combination comprises an inhibitor of the eIF4E gene product, such as ribavirin, and a chemotherapeutic agent, such as cytarabine, wherein said combination therapy overcomes resistance developed in patients during anti-neoplastic treatment. The present invention also provides for the use of a combination therapy for treating patients having a neoplasm, a proliferative disorder, pre-neoplasm or a precancerous lesion, comprising an inhibitor of the eIF4E gene product, a chemotherapeutic agent, and a therapeutically effective amount of a hedgehog pathway inhibitor, such as GDC-0449; and the method of using said combination therapy.

26 Claims, 8 Drawing Sheets

COMBINATION THERAPY USING RIBAVIRIN AS EIF4E INHIBITOR

CROSS-REFERENCE TO RELATED APPLICATIONS

This application is a national stage application of International Application No. PCT/CA2012/000831, filed Sep. 13, 2012, entitled "COMBINATION THERAPY USING RIBAVIRIN AS EIF4E INHIBITOR," which application claims the benefit of priority to Canadian Patent Application No. 2,752,008, filed Sep. 13, 2011, both of which are incorporated by reference herein in their entireties.

FIELD OF THE INVENTION

The present invention relates to use of combination therapy for treating patients having a neoplasm, a proliferative disorder, a pre-neoplasm or a precancerous lesion, comprising administering to a patient a therapeutically effective amount of an inhibitor of eukaryotic translation initiation factor 4E (eIF4E) and a therapeutically effective amount of a chemotherapeutic agent, wherein said combination treatment overcomes resistance developed in patients during anti-neoplastic treatment.

BACKGROUND OF THE INVENTION

Cancer, tumor-related disorders, and neoplastic disease states are serious and oftentimes life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm. One class of cancer is leukemia which consists of malignancies derived from hematopoietic (blood-forming) cells. Part of this class of cancers is acute myeloid leukemia (AML), also known as acute myelogenous leukemia, which is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age.

In order to treat patients diagnosed with cancer, scientific researchers around the world have investigated a multitude of mutant cancer cells, genetic mutations, site-specific mutagenesis, DNA, RNA, RNA and protein expression, transporters, genetic sequencing, so as to map biochemical pathways in cancer cells at the molecular level and find the "cure" to various types of cancer and/or the ability to manage these as chronic diseases. One of the more recent cancer research fields consists of the investigation of the deregulation of the RNA metabolism that contributes to cells becoming cancerous, and even more specifically, the inhibition of a specific factor, eukaryotic translation initiation factor 4E (eIF4E), by a well-known anti-viral drug, ribavirin, which impedes eIF4E's ability to make cells cancerous without significantly affecting normal cells.

Ribavirin is chemically designated as: 1-[(2R,3R,4S,5R)-3,4-dihydroxy-5-(hydroxymethyl)oxolan-2-yl]-1H-1,2,4-triazole-3-carboxamide, and has the following chemical structure:

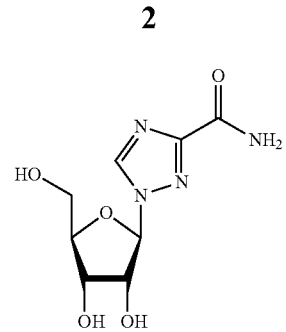

The preparation of ribavirin is disclosed in U.S. Pat. No. 3,798,209. The clinical pharmacology of ribavirin is also disclosed in Glue, "The clinical pharmacology of ribavirin" *Seminars in Liver Disease*, vol. 19, suppl. 1, 1999, p. 17-24, 1999.

Canadian Patent Nos. 2,287,056 and 2,323,849 disclose an orally administrable solid dosage form containing a compacted ribavirin composition as well as a process for making such solid dosage forms.

A further discussion on the interaction of ribavirin with eIF4E can be found in: Assouline et al., "Molecular targeting of the oncogene eIF4E in acute myeloid leukemia (AML): a proof-of-principle clinical trial with ribavirin" *Blood*, Vol. 114, no. 2 (2009); Borden, "Tissue Targeting in Cancer: eIF4E's Tale" *Clin. Cancer Res.*, 2009); Borden et al., "Ribavirin targets eIF4E dependent Akt survival signalling", *Biochem. Biophys. Res. Commun.*, Vol. 375(3): 341-345 (Oct. 24, 2008); Kraljacic, et al., "Inhibition of eIF4E with ribavirin cooperates with common chemotherapies in primary acute myeloid leukemia specimens" Leukemia 25, 1197-1200 (July 2011) and other references known in prior art.

Canadian Patent Application No. 2,685,520 discloses compounds that are useful in treating viral infections and cancer, pharmaceutical compositions comprising the compounds, and synthetic methods and intermediates that are useful for preparing the compounds. The compounds that are useful as anti-viral agents and/or anti-cancer agents include ribavirin.

Canadian Patent Application No. 2,715,885 discloses novel compounds provided for use in the treatment of tumors and the prophylaxis or treatment of viral infections, wherein one of the anti-viral agents is ribavirin.

Canadian Patent Application No. 2,674,589 discloses compounds, as well as pharmaceutical compositions comprising the compounds that are useful as anti-viral agents and/or as anti-cancer agents, wherein the one of the anti-viral agents is ribavirin.

Canadian Patent Application No. 2,430,966 discloses anilinopyrimidine derivatives as JNK pathway inhibitors and compositions comprising administering an effective amount of an anti-cancer agent, wherein one of the proposed anti-cancer agents is ribavirin or cytarabine.

The eukaryotic translation factor, eIF4E, is found in all cells and is important to make new proteins. In cancer patients, the amount of eIF4E is overexpressed in AML, and is abnormally high in 30% of cancers, including the particularly aggressive subtypes of myeloid leukemia referred to as M4 and M5. The function of eIF4E to make new proteins depends upon its ability to bind to the front part of RNA known as the m$^7$G cap (7-methyl guanosine) (located at the 5' end of the mRNA), which then allows the cell to "translate" or turn this RNA into protein. It also has a role in the export of the mRNA into the cytoplasm, which must precede the translation step. It is known in the art that cancer cells with elevated levels of eIF4E seem to have developed an oncogene addiction to eIF4E.

Examples and reference can be seen in the prior art as follows: International laid-open publication nos. WO 2007/123579 and WO 2008/060369 (Translational Therapeutics); International laid-open publication no. 2010/006291 (Nodality Inc.), and U.S. Pat. Nos. 7,425,544 and 7,601,700 and International laid-open publication no. WO 2005/028628 (Eli Lilly and Co. and ISIS Pharmaceuticals Inc.), as well as Canadian Patent Application No. 2,632,903 (Nabil-Habib Lab and Vianova Labs Inc.) and some others.

Thus, because of its properties, the eukaryotic translation factor, eIF4E, has therefore become an appealing clinical target to treat patients diagnosed with cancer, in particular AML. In this connection, targeting of the eIF4E-m$^7$G cap-binding activity has been studied in a phase II trial, in leukemia patients, and has been reported in Assouline et al., "Molecular targeting of the oncogene eIF4E in acute myeloid leukemia (AML): a proof-of-principle clinical trial with ribavirin" Blood, Vol. 114, No. 2 (Jul. 9, 2009, Epub 2009 May 11). In this trial, the commonly used anti-viral drug, ribavirin, was found to decrease the function of eIF4E because it mimics the m$^7$G cap; thus inhibiting eIF4E-induced export and translation of sensitive transcripts. In cell culture experiments, ribavirin did not modulate the levels of eIF4E protein or RNA. However in patients, ribavirin not only inhibits eIF4E, it also can lead to the downregulation of eIF4E protein (and RNA) levels as observed in patients in a phase II clinical trial using ribavirin monotherapy. Finally, in living cells, it was demonstrated that eIF4E binds $^3$H ribavirin further supporting the idea that eIF4E binds ribavirin directly in vitro and in vivo.

Several advantages have been disclosed in the prior art and from these disclosures, it can be understood that the physical mimicking of the natural ligand of eIF4E, ribavirin, preferentially inhibits the growth of primary AML (M4/M5 AML) specimens with elevated eIF4E levels relative to specimens with normal levels of eIF4E (e.g., M1/M2 AML) or normal controls. It is also taught that when ribavirin monotherapy is used, no treatment-related toxicities are observed. Further studies indicate that $^3$H ribavirin immunoprecipitates (IPs) with eIF4E in living cells further support the claim that ribavirin directly binds eIF4E.

In conducting clinical trial no. NCT00559091, the Applicant observed that many patients had resistance prior to the start of ribavirin therapy due to the other therapies they received or de novo. Also all responding patients became resistant to ribavirin monotherapy. In some patients, monotherapy had no impact suggesting that they were resistant prior to the start of treatment. Thus, a problem associated with a ribavirin monotherapy for use in cancer treatment, is that AML cells become resistant prior to the start of ribavirin therapy due to the other therapies or become resistant as a result of ribavirin treatment (primary versus acquired resistance, respectively).

In fact, leukemic cells become resistant to nearly all monotherapies within two (2) to four (4) months. To overcome this issue of resistance, it is not uncommon in the clinical field, and as for most treatments involving monotherapy, to combine such treatment, simultaneously or sequentially, with chemotherapy. The use of chemotherapeutic agents has many secondary effects on patients, including and not limited to damage of normal cells, anemia, bleeding, constipation, fatigue, hair loss, infections, memory changes, swelling, and even death, amongst many others. Conventional chemotherapy also requires a stay at the hospital so as to administer the chemotherapeutic agent(s) as well as supportive care for the side effects.

One of chemotherapeutic agents known for treating cancer is cytarabine, also known as Ara-C® (arabinofuranosyl cytosine or cytosine arabinoside), which is chemically designated as 4-amino-1-[(2R,3S,4R,5R)-3,4-dihydroxy-5-(hydroxymethyl)oxolan-2-yl]pyrim-idin-2-one. It has the following chemical formula:

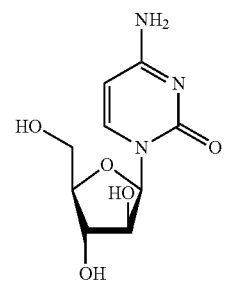

Cytosine arabinoside is a chemotherapy antimetabolic agent used mainly in the treatment of cancers of white blood cells such as acute myeloid leukemia (AML) and non-Hodgkin lymphoma. It destroys cancer cells by interfering with DNA synthesis. Its mode of action is due to its rapid conversion into cytosine arabinoside triphosphate, which damages DNA when the cell cycle holds in the S phase (synthesis of DNA). Rapidly dividing cells, which require DNA replication for mitosis, are therefore most affected. Cytosine arabinoside also inhibits both DNA and RNA polymerases and nucleotide reductase enzymes needed for DNA synthesis.

Cytosine arabinoside combines a cytosine base with an arabinose sugar. Cytosine normally combines with a different sugar, deoxyribose, to form deoxycytidine, a component of DNA. Certain sponges, where it was originally found, use arabinoside sugars to form a different compound (not part of DNA). Cytosine arabinoside is similar enough to human cytosine deoxyribose (deoxycytidine) to be incorporated into human DNA, but different enough that it kills the cell. This mechanism is used to kill cancer cells. Cytarabine is the first of a series of cancer drugs that altered the sugar component of nucleosides.

Many combinations of drugs have been developed to treat patients diagnosed with cancer, including, for example, AML. For example, Zhu et al., "Novel agents and regime for acute myeloid leukemia: 2009 ASH annual meeting highlights" Journal of Hematology & Oncology 2010, 3:17 (Review) discloses monotherapies of daunorubicin, voreloxin, ARRY-520, AZD1152, AZD6244 and terameprocol, as well as combinations of drugs such as: cytarabine with daunorubicin; fludarabine, cytarabine with idarubicin, mitoxantrone with cytarabine; clofarabine alone or in combination with low-dose Ara-C® or high dose Ara-C® with the monoclonal antibody GO; combination therapy with sorafenib; tipifarnib with bortezomib; azacitidine with bortezomib or low-dose GO; amonafile with Ara-C®; lenalidomine, Ara-C® and daunorubicin; as well as ribavirin with Ara-C®, in the treatment of elderly AML or relapsed AML or refractory AML.

The combination of ribavirin and low-dose Ara-C®, Ara-C® and idarubicin, and combinations thereof (i.e. ribavirin, Ara-C® and idarubicin) as well as sorafenib with ribavirin was specifically disclosed by Assouline et al. in "Targeting the oncogene eIF4E with ribavirin: a novel therapeutic avenue in acute myeloid leukemia" Blood 114, 2009 and by Kraljacic et al. in "Inhibition of eIF4E with ribavirin cooperates with common chemotherapies in primary acute myeloid leukemia specimens" Leukemia 25, (2011).

Clinical trials have also been conducted on several combinations of drugs for the treatment of leukemia and/or AML, and are available at: clinical trials.gov (NTC01056523) and http://clinicaltrials.gov/ct2/home.

Examples of combinations of therapy for AML, include and are not limited to: ABT-348; ABT-888 and topotecan with or without carboplatin; alemtuzumab, busulfan, and cyclophosphamide; alemtuzumab, busulfan, and melphalan; alemtuzumab with fludarabine phosphate; all-trans retinoic acid with bryostatin 1; amifostine trihydrate, cytarabine with mitoxantrone hydrochloride; arsenic trioxide; azacitidine with cytarabine (also referred to as Ara-C®); azacitidine, asparaginase, cytarabine, aunorubicin hydrochloride, etoposide, lintuzumab with thioguanine; azacitidine with arsenic trioxide; azacitidine with belinostat; azacitidine with entinostat; azacitidine with gemtuzumab ozogamicin; azacitidine with lenalidomide; azacitidine with midostaurin; 5-azacytidine (Vidaza®) with panobinostat (1bh589); 5-azacytidine (5-aza), valproic acid with all-trans retinoic acid (atra); azacytidine with valproic acid; azacitidine with phenyl butyrate; basiliximab; becatecarin; belinostat; bendamustine; bevacizumab, cytarabine with mitoxantrone hydrochloride; bexarotene and gm-csf; BMS-214662; bortezomib with belinostat; bortezomib with melphalan; bortezomib and vorinostat; bryostatin 1; busulfan, filgrastim with etoposide; busulfan with fludarabine; busulfan, cyclophosphamide, mycophenolate mofetil with tacrolimus; carboplatin, docetaxel with ifosfamide; cediranib maleate; clofarabine; clofarabine with cyclophosphamide; clofarabine, cytarabine with idarubicin; clofarabine, filgrastim with cytarabine; clofarabine and high-dose melphalan; clofarabine, melphalan, and thiotepa; cilengitide; cixutumumab with temsirolimus; CPX-151; CT53518; cytarabine and daunorubicin with or without gemtuzumab ozogamicin; cytarabine and daunorubicin with or without zosuquidar trihydrochloride; cytarabine, idarubicin with tipifarnib; cytarabine with 7-hydroxystaurosporine; cytarabine with laromustine; cytarabine with tanespimycin; cytarabine with triapine; cyclophosphamide; cyclosporine and Given IV with mycophenolate mofetil; cyclosporine, mycophenolate mofetil, and pentostatin; cyclosporine, methotrexate, methoxsalen, mycophenolate mofetil with pentostatin; decitabine; decitabine with lenalidomide; decitabine with romidepsin; decitabine with tretinoin; decitabine with valproic acid; decitabine with vorinostat (sequential); deferasirox; dolastatin; eltrombopag olamine; entinostat; everolimus; exatecan mesylate; fentanyl citrate; flavopiridol and vorinostat; fludarabine and cyclophosphamide as well as total-body irradiation, followed by cyclosporine and mycophenolate mofetil; fludarabine phosphate with Given IV; fludarabine phosphate with tretinoin; fludarabine, carboplatin, and topotecan; fludarabine, carboplatin, topotecan with thalidomide; fludarabine with melphalan; fludarabine with thiotepa; fludarabine with treosulfan; gimatecan; 7-hydroxystaurosporine with perifosine; hydroxyurea with laromustine; idarubicin with saha (vorinostat); ipilimumab; imatinib mesylate; interleukin-12 followed by interferon alfa; irofulven; itraconazole with midostaurin; ispinesib; JNJ-26481585; KW-2449; laromustine; lintuzumab; lonafarnib; MEK inhibitor AZD6244; MS-275 and gm-csf; MGCD0103; MLN8237; mycophenolate mofetil, tacrolimus with daclizumab; ON 0191 O.na; OX14503; palivizumab with or without ribavirin; paricalcitol; phenyl butyrate and tretinoin; procrit; pyroxamide; fluorouracil, leucovorin calcium, and topotecan hydrochloride; rasburicase; revlimid; romidepsin; sargramostim, amifostine trihydrate, carboplatin with cyclophosphamide; 581518; SJG-136; STA-9090; sirolimus with tacrolimus; sodium salicylate; sorafenib tosylate; sorafenib with vorinostat; tacrolimus and mycophenolate mofetil with or without sirolimus; tacrolimus and mycophenolate mofetil; tetradecanoylphorbol acetate; temsirolimus; tipifarnib; triapine with fludarabine phosphate; vorinostat; and yttrium y 90 anti-cd45 monoclonal antibody ahn-12, amongst others.

As noted in the prior art, the population having advanced AML had difficulty receiving more than one cycle of therapy. Anti-leukemia activity could be observed with relapsed/refractory disease. Another problem associated with AML drug therapies is epigenetic silencing; a phenomenon by which a drug-induced increased methylation allows for acquired drug resistance. The contribution of epigenetic mechanisms for correct cell function is highlighted by the effects of their deregulation that, in cooperation with genetic alterations, lead to the establishment and progression of tumors (see Fazi et al., in "Heterochromatic gene repression of the retinoic acid pathway in acute myeloid leukemia", Blood, May 2007, vol. 109(10), p. 4432-4440).

Other problems with concomitant drug therapy is that the drugs may produce antagonistic effects, undergo collateral sensitivity/resistance to other drugs, be difficult to determine the right dosing regimen, have toxicity issues; and create multiple drug resistance. From the above, it becomes apparent that the treatment of myelodyplastic syndromes (MDS) and/or AML remains a challenge to the clinician despite recent advances. Many patients either will not respond or will have only limited and/or brief responses to single agent therapy or even concomitant therapy.

Even in the early stage of clinical trials, some side effects have been observed, which were due to low dose Ara-C®. Hemolysis has also been observed in a patient treated with the combination of ribavirin and Ara-C®. This phenomenon can be attributed to ribavirin, but such side effects were not observed in the ribavirin monotherapy trial (NCT NCT00559091). It is possible that Ara-C® somehow potentiates this side effect. No therapy related side effects were observed with ribavirin alone.

Most virus studies have primarily focused on the effects of ribavirin on the virus, for example: mutations in viral polymerases, which is not the case in the context of the present invention. In the viral context, ribavirin impedes growth of the virus and resistance occurs when the virus continues to replicate even in the presence of ribavirin. In the cancer context, it is a measure of cells becoming resistant to the anti-proliferative effects of ribavirin, i.e. that eIF4E mediates proliferation, ribavirin impedes this effect and then eventually, the cells continue to proliferate even in the presence of ribavirin. Further, there could be different biochemical pathways modulated. Thus, one cannot compare viral infections, such as the hepatitis C virus (HCV) or the poliovirus, with cancerous type cells or cell growth as the mechanisms of action and resistance are completely different.

Drug resistance is a major impediment in cancer research, particularly for SCLC because of limited recent innovations in treatment methods. One possible explanation for chemoresistance is activation of the hedgehog signaling pathway, which promotes cellular proliferation and differentiation and has been implicated in chemoresistance. Its gene expression was examined in resistant SCLC cell lines and reported aberrant expression of hedgehog pathway-related genes, among which GLI1 was particularly significant. GLI1 is a transcription factor involved in cell fate determination, proliferation, oncogenesis, and cancer progression.

With the use of new effective chemotherapy, hormone therapy, and biological agents and with information regarding more effective ways to integrate systemic therapy, surgery, and radiation therapy, elaborating an appropriate treatment plan is becoming more complex. To offer better treatment with increased efficacy and low toxicity, selecting therapies based on the patient and the clinical and molecular characteristics of the tumor is necessary.

Therefore, accordingly a need exists to overcome the aforementioned drawbacks by a combination therapy.

SUMMARY OF THE INVENTION

It has been found that a particular combination of ribavirin (RB V) with a therapeutically effective amount of hedgehog pathway inhibitor and cytarabine (Ara-C®), or some other chemotherapeutical agent, overcomes, for the most part, the aforementioned drawbacks.

In one aspect of the present invention there is provided a pharmaceutical composition suitable for use in treating a neoplasm or a proliferative disorder, wherein the composition comprises an inhibitor of eIF4E, a hedgehog pathway inhibitor, and a pharmaceutically acceptable carrier. In a further embodiment, there is provided a pharmaceutical composition suitable for use in treating a neoplasm or a proliferative disorder, wherein the composition comprises an inhibitor of eIF4E, a hedgehog pathway inhibitor, a chemotherapeutic agent and a pharmaceutically acceptable carrier.

Another aspect of the present invention is directed to a use of a pharmaceutical composition for treating a neoplasm or a proliferative disorder, wherein the composition comprises an inhibitor of eIF4E, a hedgehog pathway inhibitor, and a pharmaceutically acceptable carrier.

In a further aspect of the present invention, there is provided a use of an inhibitor of eIF4E, a hedgehog pathway inhibitor, and a pharmaceutically acceptable carrier, for the manufacture of a medicament for the treatment of a neoplasm or a proliferative disorder.

An aspect of the present invention is directed to overcoming existing disadvantages in treatment of neoplasm, a proliferative disorder, a pre-neoplasm or a precancerous lesion by use of combination therapy, comprising an inhibitor of eIF4E and a chemotherapeutic agent to overcome resistance developed in patients during anti-neoplastic treatment.

Another aspect of the present invention is to provide a combination therapy for treating a neoplasm, a proliferative disorder, a pre-neoplasm or a precancerous lesion, comprising administering to a patient a therapeutically effective amount of an inhibitor of eIF4E with a therapeutically effective amount of a hedgehog pathway inhibitor and with or without a therapeutically effective amount of a chemotherapeutic agent, wherein said combination therapy overcomes resistance developed in patients during anti-neoplastic treatment.

An aspect of the present invention is directed to use of combination therapy for treating patients having a neoplasm or a proliferative disorder, comprising an inhibitor of eIF4E and a chemotherapeutic agent, wherein said combination therapy overcomes resistance developed in patients during anti-neoplastic treatment.

A further aspect of the present invention is directed to the use of the combination therapy for treating a neoplasm, a proliferative disorder, a pre-neoplasm or a precancerous lesion, comprising administering to a patient a therapeutically effective amount of an inhibitor of eIF4E, a therapeutically effective amount of a hedgehog pathway inhibitor with or without a therapeutically effective amount of a chemotherapeutic agent, wherein said combination therapy overcomes resistance developed in patients during antineoplastic treatment.

Another aspect of the present invention is directed to the use of combination therapy for treating patients having a neoplasm or a proliferative disorder, comprising an inhibitor of eIF4E and a chemotherapeutic agent, wherein said combination therapy minimizes or prevents the growth of resistant cells developed in patients during anti-neoplastic treatment.

Another aspect of the present invention provides a pharmaceutical composition for treating a neoplasm, a proliferative disorder, a pre-neoplasm or a precancerous lesion, wherein the pharmaceutical composition comprises an inhibitor of eIF4E, a hedgehog pathway inhibitor and a chemotherapeutic agent. Preferably the inhibitor of eIF4E is ribavirin, the inhibitor hedgehog pathway inhibitor is GDC-0449 (but similar hedgehog pathway inhibitors may also be employed), and the chemotherapeutic agent is cytarabine (Ara-C®).

Also preferably, the therapeutically effective amount of ribavirin and the therapeutically effective amount of GDC-0449 are administrated simultaneously or sequentially in resistant cells lines. More preferably the GDC-0449 is treated at 3 nM for 2 days prior to start of ribavirin treatment.

Another aspect of the present invention provides a pharmaceutical composition for treating a neoplasm, a proliferative disorder, a pre-neoplasm or a precancerous lesion, wherein the therapeutically effective amount of the inhibitor of the eIF4E gene product and the therapeutically effective amount of the hedgehog pathway inhibitor are administrated simultaneously or sequentially prior to initiating administration of the chemotherapeutic agent.

Yet another aspect of the present invention is directed to a use of combination therapy in treating the neoplasm or proliferative disorder, comprising administering to a patient a therapeutically effective amount of an inhibitor of eIF4E, a therapeutically effective amount of a hedgehog pathway inhibitor and a therapeutically effective amount of a chemotherapeutic agent, wherein said combination therapy overcomes resistance developed in patients during antineoplastic treatment.

Preferably, the inhibitor of eIF4E is ribavirin, which is administered in an amount between about 1000 to about 4400 mg per day. Also preferably, the chemotherapeutic agent is cytarabine (Ara-C®) administered in a low dose, wherein the low dose of cytarabine (Ara-C®) ranges from about 5 mg/day to about 20 mg twice a day. More preferably, the Ara-C® dose ranges between about 10 mg/day to 20 mg twice a day.

Yet another aspect of the present invention is directed to a use of an inhibitor of eIF4E, in combination therapy with a chemotherapeutic agent to overcome resistance developed in patients during anti-neoplastic treatment.

Preferably, said combination therapy comprises administering to patient a therapeutically effective amount of ribavirin, simultaneously or sequentially with a therapeutically effective amount of the cytarabine (Ara-C®).

Also preferably, said combination therapy comprises administering to the patient the therapeutically effective amount of ribavirin, wherein the plasma levels of ribavirin range from 4-10 µM, as determined by mass spectrometry. More preferably, the plasma levels of ribavirin are above 20 µM, as determined by mass spectrometry.

A further aspect of the present invention is directed to a method of use for the combination therapy for treating a neoplasm or proliferative disorder, a pre-neoplasm or a precancerous lesion, wherein said method comprises administering to patient an inhibitor of the eIF4E gene product, simultaneously or sequentially with a therapeutically effective amount of a hedgehog pathway inhibitor and with or without the chemotherapeutic agent.

A further aspect of the present invention is directed to use of combination therapy for treating a neoplasm or a proliferative disorder, wherein the treatment comprises administration of ribavirin with a chemotherapeutic agent, wherein said combination therapy reduces eIF4E levels and re-localizes the eIF4E gene product.

Preferably, the combination therapy comprises administration of an inhibitor of eIF4E in combination with a chemotherapeutic agent, wherein said combination therapy provides a collateral sensitivity to a third active agent.

DETAILED DESCRIPTION OF THE INVENTION

Figure 1:
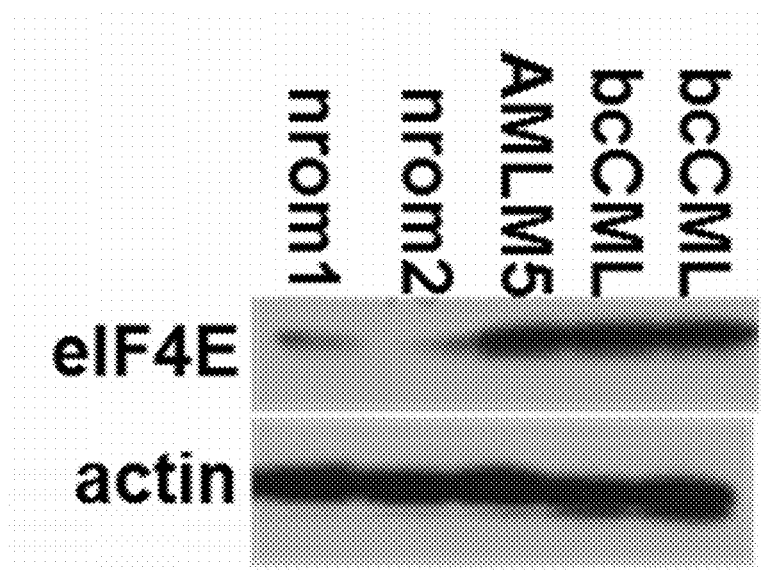
FIG. 1 is a Western analysis of CD34+ cells isolated from normal (norm), M5 AML or two blast crisis (bc) CML specimens. Actin is shown for loading. Results are representative of >100 primary specimens. It is showed that eIF4E is substantially upregulated and forms abnormally large nuclear bodies in a subset of AML (FAB subtype M4/M5) and blast crisis CML primary specimens. Further, eIF4E dependent mRNA export of targets such as cyclin D1 is substantially upregulated leading to increased protein levels for these targets.

The present invention relates to the field of pharmaceutics, and especially to use of combination therapy for treating patients having a neoplasm, a proliferative disorder, a pre-neoplasm or a precancerous lesion. In particular, the present invention is directed to the treatment of neoplasm (i.e. cancers), proliferative disorders, pre-neoplasm and pre-cancerous lesions, with a combination therapy, comprising an inhibitor of eIF4E, a hedgehog pathway inhibitor and a chemotherapeutic agent, wherein said combination therapy overcomes primary or acquired resistance developed in patients during anti-neoplastic treatment.

1. Definitions

A "prodrug" is a pharmacological substance (drug) administered in an inactive (or significantly less active) form. Once administered, the prodrug is metabolised in vivo into an active metabolite, a process termed bioactivation. The rationale behind the use of a prodrug is generally for absorption, distribution, metabolism, and excretion (ADME) optimization. Prodrugs are usually designed to improve oral bioavailability, with poor absorption from the gastrointestinal tract usually being the limiting factor. Additionally, the use of a prodrug strategy increases the selectivity of the drug for its intended target.

An example of this can be seen in many chemotherapy treatments, in which the reduction of adverse effects is always of paramount importance.

The abbreviation "eIF4E" stands for eukaryotic translation initiation factor 4E, which is a protein which in humans is encoded by the eIF4E gene product.

By an "inhibitor of eIF4E" as used herein, is meant any compound that inhibits the biochemical activity of the eIF4E gene product including its role in mRNA translation and mRNA export or eIF4E levels (RNA or 25 protein). An example of inhibitors of eIF4E is ribavirin (1-13, 0-ribofuranosyl-1 H-1,2,4-triazole-3-carboxamide) and its derivatives. Preferably, an "inhibitor of eIF4E" results in a reduction in cancer or dissemination of, for example, at least 10%, 20%, 30%, 40% or 50%. In more preferable embodiments, an "inhibitor of eIF4E" reduces replication or dissemination, for example, by at least 60%, 70%, 80%, 90%, 95%, or even 99%, of cancer cells.

The term "GDC-0449" means the inhibitor of Hedgehog-Gli pathway which is developed for potential use in cancer treatment. GDC-0449 is a small-molecule inhibitor designed to specifically inhibit SMO, a key mediator of the Hh signaling pathway. GDC-0449 was discovered by Genentech and was jointly validated with Curis, Inc. through a series of preclinical studies.

The term "chemotherapeutic agent" as used herein, means a drug used in treatment of cancer usually an antineoplastic drug or with a combination of such drugs into a standardized treatment regimen. Most chemotherapy agents and medications work by interfering with DNA synthesis or function. Based on their chemical action at a cellular level, chemotherapy agents can be classified as cell-cycle specific agents (effective during certain phases of cell cycle) and cell-cycle nonspecific agents (effective during all phases of cell cycle).

Depending on their characteristics and nature of treatment, chemotherapy agents can be categorized as alkylating agents, antimetabolites, anthracyclines, antitumor antibiotics, monoclonal antibodies, platinums, or plant alkaloids.

The term "low dose" as referred to herein, means an amount of Ara-C® for repressing the tumorgenicity of cells.

The terms "cancer", "cancerous" or "neoplasm" or "neoplastic cells" comprises neoplasm, cancers, or neoplastic cells located at the original site of proliferation ("primary tumor or cancer") and their invasion of other tissues, or organs. They also refer to or describe the physiological condition in mammals in which a population of cells is characterized by unregulated cell growth.

Examples of cancer include and are not limited to: leukemia, acute myeloid leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma, Hodgkin's disease, non-Hodgkin's disease lymphoma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lyinphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma (SCLC), bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma, lung cancer, squamous cell carcinoma, adenocarinoma, large cell carcinoma, colorectal cancer, ovarian cancer, ovarian adenocarcinoma, prostate cancer, myelodysplastic syndromes (MDS) and multiple myeloma.

The term "neoplasm" or "neoplastic" also means a cell or tissue exhibiting abnormal growth, including hyperproliferation or uncontrolled cell growth, that may be benign or cancerous. The development from a normal cell to a cell exhibiting a neoplastic phenotype is a multi-step process. Cells developing a neoplastic phenotype or designated as of a cancerous cell type generally exhibit an alteration of the normal cell cycle and altered cell death response. Generally, the changes that a cell undergoes in developing to a tumor cell may be monitored at the cellular or DNA level.

Therefore, the terms "pre-neoplasm" or "pre-neoplastic" phenotype are construed for the purposes of the present invention to refer to a cell or tissue which exhibits changes at the DNA or cellular level that evidence the ultimate progression of the cell or tissue to a neoplastic or cancerous phenotype. Pre-neoplastic conditions do not show evidence of microinvasion or other hallmarks of cancer behavior. As with the development to neoplasia, pre-neoplastic cells may exhibit progression through multiple steps. Although a pre-neoplastic cell may progress to a neoplastic stage, they may remain stable for an extended period of time and may even regress. The development of pre-neoplasia is often associated with environmental factors. Examples of pre-neoplastic conditions in noninvasive bladder cancer include diffuse cellular atypia of the urothelium.

The term "proliferative disorder" refers to disorders that are associated with some degree of abnormal cell proliferation.

The term "precancerous" refers to cells or tissues having characteristics relating to changes that may lead to malignancy or cancer. Examples include adenomatous growths in colon, ovary, breast, tissues, or conditions, for example, dysplastic nevus syndrome, a precursor to malignant melanoma of the skin. Examples also include, abnormal neoplastic, in addition to dysplastic nevus syndromes, polyposis syndromes, prostatic dysplasia, and other such neoplasms, whether the precancerous lesions are clinically identifiable or not.

A "precancerous lesion(s)" may refer to an epithelial precancerous lesion, which is a skin lesion that has a propensity to develop into a cancerous condition. Epithelial precancerous skin lesions also arise from other proliferative skin disorders such as hemangiomas, keloids, eczema and papilloma virus infections producing verruca vulbaris, verruca plantaris and verruca planar.

The symptoms of the epithelial precancerous lesions include skin-colored or red-brown macule or papule with dry adherent scales. Actinic keratosis is the most common epithelial precancerous lesion among fair skinned individuals. It is usually present as lesions on the skin which may or may not be visually detectable. The size and shape of the lesions varies. It is a photosensitive disorder and may be aggravated by exposure to sunlight. Bowenoid actinic keratosis is another form of an epithelial precancerous lesion. In some cases, the lesions may develop into an invasive form of squamous cell carcinoma and may pose a significant threat of metastasis. Other types of epithelial precancerous lesions include hypertrophic actinic keratosis, arsenical keratosis, hydrocarbon keratosis, thermal keratosis, radiation keratosis, viral keratosis, Bowen's disease, erythroplaquia of queyrat, oral erythroplaquia, leukoplakia, and intraepidermal epithelialoma.

By "inhibits the growth of a neoplasm" is meant measurably slowing, stopping, or reversing the growth rate of the neoplasm or neoplastic cells in vitro or in vivo. Preferably, a slowing of the growth rate is by at least 20%, 30%, 40%, 50%, 60% or even 70% is achieved, over a period of treatment of six month as determined using a suitable assay for determination of cell growth rates (e.g., a cell growth assay described herein). Typically, a reversal of growth rate is accomplished by initiating or accelerating necrotic or apoptotic mechanisms of cell death in the neoplastic cells, resulting in shrinkage of the neoplasm.

The term "complete molecular response" means that molecular response as the eIF4E gene product moving and going down (at least in leukemia-responses may be different in other cancers i.e. cancers with less nuclear eIF4E may not have pronounced movement to the cytoplasm etc.). Targeting eIF4E activity should also be there (looking at export and translation targets); In leukemia as referred to herein, means complete molecular response as eIF4E moving, eIF4E going down and targeting the eIF4E gene product function.

By "an effective amount", "a neoplasm treating amount", "a pre-neoplasm treating amount", "a proliferative treating amount" or by "a precancerous lesion treating amount" is meant the amount of a compound or a combination of compounds required to treat or prevent a disease in a clinically relevant manner. An effective amount or a treating amount of a compound varies depending upon the disease being treated, the manner of administration, and the age, body weight, and general health of the patient. Ultimately, the prescribers will decide the appropriate amount and dosage regimen according to good medical practice.

The term "therapeutically effective amount" intends to describe concentrations or amounts of compounds according to the present invention which are therapeutically effective in treating neoplasm (I.e. tumors, cancers, etc.), pre-neoplasm, proliferative disorders, and/or precancerous lesions or the various conditions or disease states including hyperproliferative cell growth.

The term "effective amount" shall mean an amount or concentration of a compound or composition according to the present invention which is effective within the context of its administration, which may be inhibitory, prophylactic and/or therapeutic. Compounds according to the present invention are particularly useful for providing favorable change in the disease or condition treated, whether that change is a remission, a decrease in growth or size of cancer or a tumor or other effect of the condition or disease to be treated, a favorable physiological result or a reduction in symptomology associated with the disease or condition treated.

The term "administering" refers to a method of giving a composition of the invention to a patient, by a route such as inhalation, ocular administration, nasal instillation, parenteral administration, dermal administration, transdermal administration, buccal administration, rectal administration, sublingual administration, perilingual administration, nasal administration, topical administration and oral administration. Parenteral administration includes intrathecal, intraarticular, intratumoral, intravenous, intraperitoneal, subcutaneous, and intramuscular administration. The optimal method of administration of a drug or drug combination to treat a particular disease can vary depending on various factors, e.g., the oral bioavailability of the drug(s), the anatomical location of the disease tissue, and the severity of disease.

The hedgehog (Hh) signaling pathway plays an important role in embryogenesis across multiple species. Its activity is reduced or absent in adult organisms. However, activation of the pathway has been shown to be a factor in the development of a number of human malignancies and inhibition of the pathway is being investigated as a potential treatment for multiple cancers.

The term 'western blot" refers to the analysis of protein(s) (or polypeptides) immobilized onto a support such as nitrocellulose or a membrane. The proteins are run on polyacrylamide gels to separate the proteins, followed by transfer of the protein from the gel to a solid support, such as nitrocellulose, polyvinylidene fluoride (PVDF) or a similar membrane. The immobilized proteins are then exposed to antibodies with reactivity against an antigen of interest. The binding of the antibodies can be detected by various methods, including the use of radio-labeled antibodies or chemiluminescence.

Other features and advantages of the invention will be apparent from the following detailed description, the drawings, and the claims.

2. Pharmacological Inhibition of eIF4E by Ribavirin

Ribavirin has been found to act as a competitive inhibitor of the $m^7G$ cap and thereby inhibiting eIF4E functions in both the export and translation of sensitive transcripts. NMR, fluorescence, and mass spectrometry studies indicate that ribavirin directly binds eIF4E. $^3H$ ribavirin binds to eIF4E in living cells as shown by the 14-fold enrichment of $^3H$ ribavirin in eIF4E immunoprecipitations relative to controls. The active metabolite of ribavirin, ribavirin triphosphate (RTP), binds eIF4E with a similar affinity as $m^7GTP$ and impedes mRNA export of eIF4E targets and translation of vascular endothelial growth factor (VEGF) and ornithine decarboxylase (ODC) but not the export or translation of eIF4E insensitive transcripts such as glyceraldehyde 3-phosphate dehydrogenase (GAPDH). Ribavirin sensitivity parallels eIF4E sensitivity and inhibits both the nuclear and cytoplasmic functions of eIF4E. Importantly, ribavirin affects primary AML specimens with elevated eIF4E more than specimens with normal eIF4E levels. In total, it appears that these AML specimens have developed an "oncogene addiction" to eIF4E making them more sensitive to inhibition of eIF4E than specimens with normal eIF4E levels. The clinical utility of ribavirin treatment in M4/M5 AML patients was investigated.

The effectiveness of chemotherapy is limited in some cases because the leukemia cells become resistant to it or have a resistance due to prior therapies or a de novo resistance (primary). As discussed above, the Applicant tested the efficacy of ribavirin treatment in patients in a Canada-wide clinical trial, and observed striking improvement with the patients, however, all eventually developed resistance to ribavirin (Assouline et al., *Blood*, 2009).

Usually, chemotherapy is given in cycles, with each period of treatment followed by a rest period to allow the body time to recover. Therefore, researchers are looking at ways to prevent or reverse this resistance by using other drugs along with chemotherapy.

3. Cooperation Between the Inhibitor of eIF4E and the Hedgehog Pathway Inhibitor The eukaryotic translation initiation factor eIF4E gene is elevated in M4 and M5 acute myeloid leukemia (AML). The oncogenic potential of eIF4E depends on its ability to bind the $m^7G$ cap on the 5' end of mRNAs. Applicant discovered that ribavirin acts as a competitive inhibitor of the cap thereby inhibiting eIF4E's activities. The phase II ribavirin monotherapy trial in poor prognosis AML patients demonstrated that ribavirin treatment targeted the eIF4E gene product activity and this correlated with clinical benefit including remissions. To improve clinical outcomes, the features that lead to primary and acquired ribavirin resistance were examined as were heterogeneity in patient response, assessing new contexts for ribavirin use and determining the efficacy of combining ribavirin with a hedgehog pathway inhibitor and/or with low dose cytarabine (Ara-C®) in patients.

To overcome the resistance problem due to prior antineoplastic therapies or a de novo resistance in the treatment with ribavirin, and according to the present invention, there is provided a combination therapy for treating patients having an affliction selected from the group consisting of: a neoplasm, a pre-neoplasm, a proliferative disorder, and a precancerous lesion.

To improve clinical outcomes by acquired ribavirin resistance, heterogeneity in patient's response and resistance in patient specimens was explored. In a preferred embodiment, the inventors assessed new contexts for ribavirin use, including the efficacy of combining an inhibitor of the eIF4E gene product with a hedgehog pathway inhibitor and/or a chemotherapeutic agent in patients.

Two distinct mechanisms were identified underlying resistance. First, ribavirin uptake is impaired through loss of its nucleoside transporter and/or adenosine kinase. Second, elevation of the sonic hedgehog transcription factor Gli-1 leads to activation of UGT1A enzymes and subsequent glucurondiation of ribavirin, thereby preventing its association with eIF4E. Gli-1 overexpression is sufficient to impart resistance. Genetic knockdown of Gli-1, or pharmacological inhibition of Gli-1 with GDC-0449, reverts resistance, correlating with reappearance of ribavirin-eIF4E complexes. In patient specimens, clinical resistance correlated with elevated Gli-1 levels. Thus, resistance to a targeted therapy can be driven by chemical modification of the drug rather than solely by mutation of the target protein. Gli-1 also has proliferative capacity and could drive oncogenesis independently of eIF4E in resistant cells due to genetic re-wiring.

The combination therapy according to the present invention comprising an inhibitor of eIF4E, a hedgehog pathway inhibitor and/or a chemotherapeutic agent overcomes the resistance developed in patients during anti-neoplastic treatment.

The effects of the combined treatment of an inhibitor of eIF4E, preferably ribavirin with a hedgehog pathway inhibitor, preferably GDC-0449, were examined. GDC-0449 is a small molecule inhibitor of Hedgehog-Gli pathway being developed for potential use in cancer treatment.

As discussed above, Gli-1 lead to the loss of ribavirin-eIF4E interaction and thus resistance in F10R cells, that the UGT1A family of proteins was highly elevated. The Applicant has examined that there is a link between Gli-1 and UGT and that this leads to glucurondiation of ribavirin, losing the interaction. The applicant has examined pretreating the F10R cells with GDC-0449 and then adding the ribavirin.

The applicant has examined whether the inhibitor of eIF4E, preferably ribavirin and a hedgehog pathway inhibitor, preferably GDC-0449, cooperated in poor prognosis AML patient specimens.

According to the present invention, novel combinatory drug therapy is useful due to the cooperation between the inhibitor of eIF4E, the hedgehog pathway inhibitor, and, if necessary, the chemotherapeutic agent, which destroys cancer cells by interfering with DNA synthesis.

4. Cooperation Between the Inhibitor of eIF4E and the Chemotherapeutic Agent Several models of collaboration between these drugs was determined, namely:
Ribavirin inhibits eIF4E functions and cytarabine (Ara-C®) interferes with nucleic acid synthesis or nucleotide synthesis, being an inhibitor of DNA polymerase and blocking DNA synthesis, but having no effect on RNA or protein synthesis;
Cytarabine incorporated into RNA and DNA interfering with chain elongation; ribavirin acts as a competitive inhibitor of the $m^7G$ cap;
Cytarabine (Ara-C®) is cytotoxic and is highly specific for the S phase of the cell cycle, whereas ribavirin is cytostatic;
Cytarabine (Ara-C®) can increase ribavirin's inhibition of its targets by either blocking proper 5'cap formation on these mRNAs and/or by incorporating into cellular RNAs and further inhibiting their translation or export;
Cytarabine (Ara-C®) exhibits cell phase specificity, primarily killing cells undergoing DNA synthesis (S-phase) and under certain conditions blocking the progression of cells from the G1 phase to the S-phase (The Extra Pharmacopoeia, 30th ed); and
Ribavirin induces a G1/S arrest in many cell types (Kentsis et al., 2004). Thus, ribavirin can collaborate in this way with cytarabine (Ara-C®).

The effects of the combined treatment of an inhibitor of eIF4E, preferably ribavirin with an antimetabolite, preferably cytarabine (Ara-C®), have been examined. Cytarabine (Ara-C®) is a pyrimidine nucleoside analog that inhibits the synthesis of DNA, and has shown specificity for the S phase of the cell cycle. It is metabolized intracellularly into its active triphosphate form (cytosine arabinoside triphosphate). Further this metabolite damages DNA by multiple mechanisms, including the inhibition of alpha-DNA polymerase, inhibition of DNA repair through an effect on beta-DNA polymerase, and incorporation into DNA.

The Applicant has examined whether the inhibitor of eIF4E, preferably ribavirin and a chemotherapeutic agent, preferably cytarabine (Ara-C®) cooperated in poor prognosis AML.

It is not uncommon in cancer treatments to have mixtures of three or more drugs. In this connection, other agents may be used in conjunction with the combination of inhibitor of eIF4E and the hedgehog pathway inhibitor. For example, the composition according to the present invention may further comprise at least another pharmaceutically active substance. Other pharmaceutically active substance(s), include, and are not limited to: topoisomerase inhibitors, NFKB inhibitors, hedgehog pathway inhibitors, methyltransferase inhibitors, etc.

Preferably, the inhibitor of eIF4E is ribavirin, the hedgehog pathway inhibitor is GDC-0449 and the chemotherapeutic agent is selected from the category of antimetabolites, more preferably, from the class of pyrimidine antagonists, and most preferably, is cytarabine (Ara-C®).

5. Indications for Treatment

The compositions of the present invention are preferably aimed at treating conditions which involve undesirable or uncontrolled cell proliferation. Such conditions include neoplasms, pre-neoplasms, proliferative disorders and precancerous lesions. In a preferred embodiment, the neoplasm is cancer.

Preferably, the cancer is selected from the group consisting of leukemia, acute myeloid leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma, Hodgkin's disease, non-Hodgkin's disease lymphoma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lyinphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma, lung cancer, squamous cell carcinoma, adenocarcinoma, large cell carcinoma, colorectal cancer, ovarian cancer, ovarian adenocarcinoma, prostate cancer, myelodysplastic syndromes, and multiple myeloma.

According to the present invention, the acute myeloid leukemia is acute myeloid leukemia M4 or acute myeloid leukemia M5 or another AML subtype characterized by atypical elevation of the e1F4E gene product.

Other types of cancers which could be potentially treated include but are not limited to leukemia, acute myeloid leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma, Hodgkin's disease, non-Hodgkin's disease lymphoma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lyinphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, retinoblastoma, lung cancer, squamous cell carcinoma, adenocarinoma, large cell carcinoma, colorectal cancer, ovarian cancer, ovarian adenocarcinoma, prostate cancer, myelodysplastic syndromes and multiple myeloma.

Generally, cells in a benign tumor retain their differentiated features and do not divide in a completely uncontrolled manner. A benign tumor is usually localized and non metastatic. Specific types of benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor, cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, or even infiltrating leukemia cells, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.). Malignant leukemia cells can infiltrate into other tissues.

Specific types of cancers or malignant tumors, either primary or secondary, that can potentially be treated using the present invention include leukemia, breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells, which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes (MDS), multiple myeloma and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15; 17 chromosomal translocation. This translocation leads to the generation of the fusion transcript comprised of the retinoic acid receptor and the PML gene product.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9; 22 translocation. The resultant Philadelphia chromosome represents poor prognosis of the patient. Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML. Chronic phase CML is often successfully treated with Gleevec®. However, when this converts to blast crisis CML, Gleevec® is not effective. Our previous studies indicate that eIF4E levels are elevated in blast crisis CML, but not in the chronic phase.

This means that blast crisis CML patients could be candidates for the combination therapy according to the present invention.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia. MDS patients could be candidates for this therapy.

6. Routes of Administration and Dosing Regimen

A number of routes of administration and formulations may be used in the combination therapies of the present invention. The combination of therapeutic treatment according to the present invention may be administered in combination with one or more conventional pharmaceutical agents.

These additional agents may include additional compounds according to the invention, or one or more other pharmaceutically active agents.

The compound may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. More particularly, other forms of administration include, for example: inhalation, ocular administration, nasal instillation, parenteral administration, dermal administration, transdermal administration, buccal administration, rectal administration, sublingual administration, perilingual administration, nasal administration, topical administration, and oral administration.

The compounds according to the present invention may also be administered or co-administered, sequentially or simultaneously, in immediate release, delayed release or even slow release dosage forms.

The inhibitor of eIF4E, the hedgehog pathway inhibitor, and the chemotherapeutic agent, according to the present invention, are administered sequentially or simultaneously. The compound according to the present invention may be administered by a variety of routes, and may be administered or co-administered in any conventional dosage form.

The composition, according the present invention, is in a unit dosage form. Co-administration in the context of this invention is defined to mean the administration of more than one therapeutic in the course of a coordinated treatment to achieve an improved clinical outcome. Such co-administration may also be coextensive, that is, occurring during overlapping periods of time. For example, the chemotherapeutic agent may be administered to a patient before, concomitantly, or after the inhibitor of eIF4E is administered. In a preferred embodiment, the patient may be pretreated with the hedgehog pathway inhibitor and then treated with the inhibitor of eIF4E (e.g., ribavirin).

The amounts of the therapeutic agents present in the compositions can vary, according to determinations made by a person skilled in the art, but preferably are in amounts effective to create a cytotoxic or cytostatic effect at the desired site. Preferably, these total amounts are less than the total amount adding the maximum tolerated dose for each of the Ara-C®, the eIF4E inhibitor, and the hedgehog pathway inhibitor, and more preferably less than the total amount added for individual administration of each of these inhibitors. In a preferred embodiment, the amount of therapeutic agent(s), i.e., an inhibitor of eIF4E, hedgehog pathway inhibitor and/or a Ara-C® are deemed to be in an effective amount for treating the indication, for example: a neoplasm (i.e. cancer or, more particularly, acute myeloid leukemia), a pre-neoplasm, a proliferative disorder, or a precancerous lesion. Preferably, for the dosage form, appropriate release times can vary, but preferably should last from about 1 hour to about 6 months and most preferably from about 1 week to about 4 weeks. Formulations including the compositions according to the present invention can vary, as determinable by a person skilled in the art, according to the particular situation, and as generally taught herein.

In a preferred embodiment, the inhibitor of eIF4E (preferably ribavirin) is administered in an amount between about 500 mg to 4400 mg per day, and more preferably, in the range between about 1000 mg to about 4400 mg per day. The hedgehog pathway inhibitor, such as GDC-0449, is preferably administered at 3 nM for 2 days prior to the start of ribavirin treatment. The Ara-C® is preferably administered in an amount up to about 100 mg/m$^2$. This administration can preferably last for up to 7 days every 4 weeks, on a repetitious basis if required. Preferably, the Ara-C® is administered in an amount sufficient to repress tumorgenicity of cells. More preferably, the Ara-C® is administered in a low dose. In this connection, a low dose of Ara-C® preferably ranges from about 5 mg/day to about 20 mg twice a day.

Also according to an embodiment of the present invention, after the treatment with GDC-0449 and ribavirin, the patient may be further treated with Ara-C® and various anticancer agents described above.

According to the present invention, there is provided a method to administer to a patient a therapeutically effective amount of an inhibitor of eIF4E, a therapeutically effective amount of a hedgehog pathway inhibitor and a therapeutically effective amount of a chemotherapeutic agent.

Preferably, the hedgehog pathway inhibitor is GDC-0449, using 3 nM which was reported to be the plasma levels according to Roche.

More preferably, a therapeutically effective amount of the inhibitor of eIF4E and the therapeutically effective amount of GDC-0449 are administrated simultaneously or sequentially in resistant cell lines.

According to the present invention, there is provided a method to administer to a patient a therapeutically effective amount of the inhibitor of eIF4E and the therapeutically effective amount of the hedgehog pathway inhibitor prior to initiating administration of the chemotherapeutic agent. Preferably, the inhibitor of eIF4E and said hedgehog pathway inhibitor are administrated concurrently with the chemotherapeutic agent. Also preferably, the inhibitor of eIF4E and said hedgehog pathway inhibitor are administrated sequentially with the chemotherapeutic agent.

According to the present invention, there is provided a method to administer to treat a patient with a combination therapy for treating patients having a neoplasm or a proliferative disorder, comprising administering to a patient a therapeutically effective amount of the hedgehog pathway inhibitor in the presence of a therapeutically effective amount of ribavirin wherein said combination therapy reverts resistance developed in patients during anti-neoplastic treatment or in patients with primary resistance.

Owing to the sensitizing effects of the combination therapy on the cells to cell death or senescence or some permanent cell cycle arrested state, the dosage of anticancer agents used for the treatment may be lower than that used in a conventional cancer treatment regimen. Thus, a better clinical outcome may be achieved by using the compositions and methods of the present invention.

The present invention provides for:
- the use of combination therapy for treating patients having a neoplasm or a proliferative disorder, comprising an inhibitor of the eIF4E gene product, a hedgehog pathway inhibitor, and a chemotherapeutic agent, wherein said combination therapy overcome resistance developed in patients during anti-neoplastic treatment;
- the use of combination therapy in treating the neoplasm or proliferative disorder comprising administering to a patient a therapeutically effective amount of an inhibitor of the eIF4E gene product, a therapeutically effective amount of a hedgehog pathway inhibitor with or without a therapeutically effective amount of a chemotherapeutic agent;
- a method of use for a combination therapy in treating patients having a neoplasm or a proliferative disorder, comprising an inhibitor of the eIF4E gene product and the chemotherapeutic agent, wherein said combination therapy overcomes resistance developed in patients during anti-neoplastic treatment;
- a method of use a combination therapy for treating a neoplasm or a proliferative disorder, wherein said method comprises administering a therapeutically effective amount of an inhibitor of the eIF4E gene product, a therapeutically effective amount of a hedgehog pathway inhibitor and a therapeutically effective amount of a chemotherapeutic agent, wherein said combination therapy overcomes resistance developed in patients during anti-neoplastic treatment from previous therapies, from ribavirin therapy or de novo;
- the use of combination therapy for treating patients having a neoplasm or a proliferative disorder, comprising an inhibitor of the eIF4E gene product, a hedgehog pathway inhibitor and a chemotherapeutic agent, wherein said combination therapy minimizes or prevents the growth of resistant cells developed in patients during anti-neoplastic treatment; inhibition of the hedgehog pathway to revert resistance and/or decrease proliferation; and
- a method of use of a combination therapy for treating a pre-neoplasm or a precancerous lesion, wherein said method comprising administering a therapeutically effective amount of an inhibitor of the eIF4E gene product, a therapeutically effective amount of a hedgehog pathway inhibitor and a therapeutically effective amount of a chemotherapeutic agent, wherein said combination therapy overcome resistance developed in patients during anti-neoplastic treatment from previous therapies, from ribavirin therapy or de novo.

In a preferred embodiment, the preneoplasm or precancerous lesion is selected from the group consisting of: proliferative disorders that lead to the development of solid or hematological neoplasms and preneoplasms or precancerous lesions that may evolve into a neoplasm.

The following examples are intended to illustrate, but not limit the invention.

EXAMPLES

According to the present invention, there is provided a use of a combination therapy for treating patients having a neoplasm, proliferative disorder, pre-neoplasm or precancerous lesion comprising an inhibitor of eIF4E, a hedgehog pathway inhibitor, and a chemotherapeutic agent, wherein said combination therapy overcomes resistance developed in patients during anti-neoplastic treatment from previous therapies, from ribavirin therapy or de novo.

The treatment comprises administering a therapeutically effective amount of ribavirin, as an inhibitor of the eIF4E gene product; administering a therapeutically effective amount of a hedgehog pathway inhibitor, which is GDC-0449; and administering a therapeutically effective amount of chemotherapeutic agent, which is cytarabine, (Ara-C®).

The patients can be administered at least between 500 mg/day to 4400 mg/day of ribavirin and at least between 50 mg/m×sup×2 to 150 mg/m×sup×2 of cytarabine. More preferably, a patient can be administered at least between 1000 and 2800 mg/day of ribavirin and up to 100 mg/m×sup×2 of cytarabine. In even a more preferred embodiment, the inhibitor of eIF4E is administered in an amount between 1000 to 4400 mg per day and the cytarabine (Ara-C®) is administered in an amount from 10 mg/day to 20 mg twice a day.

The effects of either drug treatment alone or in combination, for AML specimens, is disclosed hereinabove as well as in FIG. 1. The eIF4E gene product is substantially up-regulated and forms abnormally large nuclear bodies in a subset of AML (FAB subtype M4/M5) and blast crisis CML primary specimens (FIG. 1).

Further, eIF4E dependent mRNA export of targets such as cyclin D1 is substantially up-regulated leading to increased protein levels for these targets and subsequent proliferation.

Phase II Ribavirin Monotherapy Trial in Poor Prognosis AML Patients

Ribavirin treatment targeted the eIF4E gene product activity in patients with relapsed/refractory M4/M5 AML or who were deemed unable to undergo standard chemotherapy.

In terms of clinical response, 1 CR (complete remission), 2 PR (partial remission), 3 BR (blast response), 6 SD (stable disease), 3PD (progressive disease) were observed out of 15 evaluable patients. No drug related toxicity was observed in any of the patients. The molecular analyses indicated that ribavirin treatment targeted the eIF4E gene product activity and this correlated with response. For instance, the mRNA export activity of the eIF4E gene product was directly monitored and it was shown that, after 28 days of oral ribavirin, this was substantially reduced. A biphasic molecular response was observed, where initially the eIF4E gene product was dramatically re-distributed to the cytoplasm in patients that responded. This was followed by a drop in eIF4E RNA and protein levels (up to one 28 day cycle). This conclusively supports that ribavirin directly targets the eIF4E gene product activity in patients and this correlated with clinical benefit. However, all responding patients eventually became resistant to ribavirin.

Phase I Ribavirin and Low Dose Ara-C® Trial in Poor Prognosis AML

Phase I trial was carried out to establish the safety of a combination of oral ribavirin and subcutaneous low dose Ara-C® in the same patient population. These compounds cooperated in colony growth assays of primary specimens. Ara-C® was kept constant (except in case of toxicity) and ribavirin doses elevated in a 3+3 trial design for the phase I arm. In the first dose level, it was noted that ribavirin plasma levels were substantially lower than was observed in the monotherapy trial. As known from prior art, other oral compounds also had their absorption reduced by subcutaneous Ara-C® including digoxin.

In the monotherapy trial at 2000 mg/day of ribavirin, plasma levels of around 20-30 µM ribavirin (determined by mass spectrometry) were achieved, which corresponded to a therapeutic range whereas in the combination trial ribavirin plasma levels ranged from only 4-10 µM. In the monotherapy trial at 2800 mg/day, plasma levels of 20 µM ribavirin were achieved.

In phase I combination trial, 5 patients achieved plasma levels of 20 µM ribavirin or higher. Of these, has been observed a complete molecular response for the CR, BR, SD and none for the 2 PD indicating that ribavirin levels were sufficient to effect the eIF4E gene product localization and levels. The CR had secondary AML due to breast cancer therapy and had some toxicities due to Ara-C®, and thus the Ara-C® levels were lowered to 10 mg/day. This correlated with a near doubling of plasma ribavirin levels and achievement of CR. After 6 cycles, Ara-C® was discontinued and patient remains in CR on ribavirin alone for the past twelve cycles (totalling 18 cycles).

Heterogeneity in Patient Response

It was observed that patients from both trials that had a complete molecular response to ribavirin (lowering of the eIF4E levels after an initial relocalization of the eIF4E gene product) achieved CR, PR, BR or SD (but NOT PD). This heterogeneity suggests that eIF4E is more central in driving the leukemia of the best responding patients than others. This is consistent with the theory that the entire leukemia cell population has not coupled its survival to the same signalling pathways. Patients with a greater number of eIF4E dependent leukemia cells would be expected to respond better. There is the distinct possibility that other pathways are needed to cooperate with the eIF4E gene product to transform cells and the nature of these pathways may be heterogeneous and differentially affect ribavirin response. The sonic hedgehog pathway is one such pathway.

It was also observed that there was no correlation between Flt3 or NPM status and response. Alternatively or in addition, some patients (who are mostly heavily pre-treated) may be on the verge of resistance when they enter the trial and that ribavirin treatment leads to a final selection of a resistant population in terms of the ENT1 nucleoside transporter, used by both ribavirin and Ara-C®.

Ribavirin Heterogeneity

To understand the heterogeneity in clinical response, it is critical to study patient specimens to monitor changes in gene expression as a function of treatment, response, and resistance.

Heterogeneity in response and resistance in patient specimens was explored. The gene expression profile of a variety of patient specimens was examined by deep sequencing to assess differences before treatment, during response, and at relapse as well as comparing responders to non-responders.

Factors that contribute to resistance in resistant cell lines were examined and candidates from these studies were monitored in patient specimens. Such markers should help predict which patients are most/least likely to benefit from ribavirin treatment. Deep sequencing analysis revealed that Gli-1, the sonic hedgehog transcription factor, was highly elevated in cell lines that had normal uptake of ribavirin, but had no ribavirin response in terms of growth or the eIF4E gene product activity. Indeed in these cells, the ribavirin-eIF4E interaction was lost despite the fact that the eIF4E gene product was not mutated.

Ribavirin Resistance Correlates with Loss of eIF4E Targeting

Figure 4:
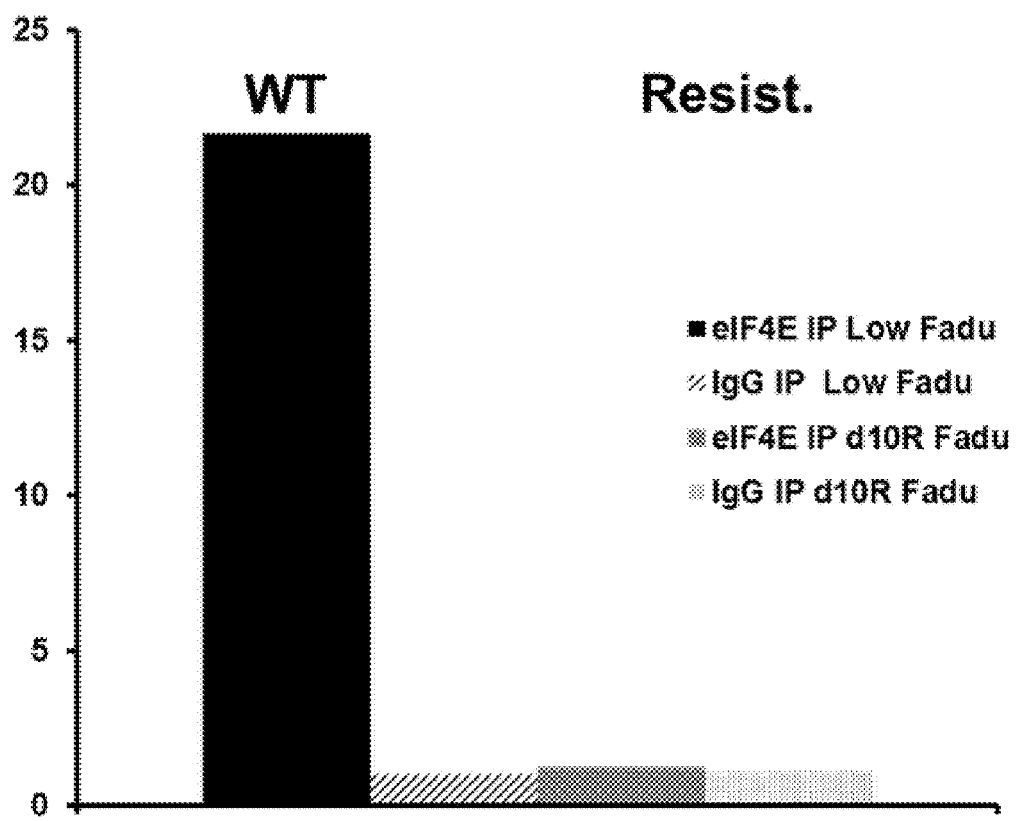
FIG. 4 is a diagram showing Type II resistance: Normal uptake, loss of eIF4E-ribavirin interaction. Fold enrichment of 14C ribavirin over negative control (IP IgG).

It was assessed whether ribavirin is still targeting eIF4E activity in resistant cells (FIG. 4). Protein levels of well-established eIF4E mRNA export and translation targets, including cyclin D1 and VEGF were monitored as a function of ribavirin treatment. In parental cell lines, ribavirin treatment reduces levels of these proteins whereas in resistant cell lines, ribavirin treatment no longer affects these. There was no change in the total levels of eIF4E between resistant and parental cell lines, as observed in other cell line systems.

It was determined whether $^{14}$C-ribavirin could immunoprecipitate with eIF4E in the F10R and F100R resistant cell lines. It is noted that the $^{14}$C or $^{3}$H label is at position 5 of the triazole ring i.e. the active moiety of ribavirin. In parental cell lines, $^{14}$C ribavirin is enriched in the eIF4E immunoprecipitated fraction by about 20 fold relative to the IgG control, whereas $^{14}$C ribavirin does not immunoprecipitate with eIF4E in the F10R or F100R cell lines (FIG. 4). Sequencing analysis indicated that there were no mutations in the coding region of eIF4E in F10R and F100R cells.

Defects in Ribavirin Uptake and Metabolism

Figure 5:
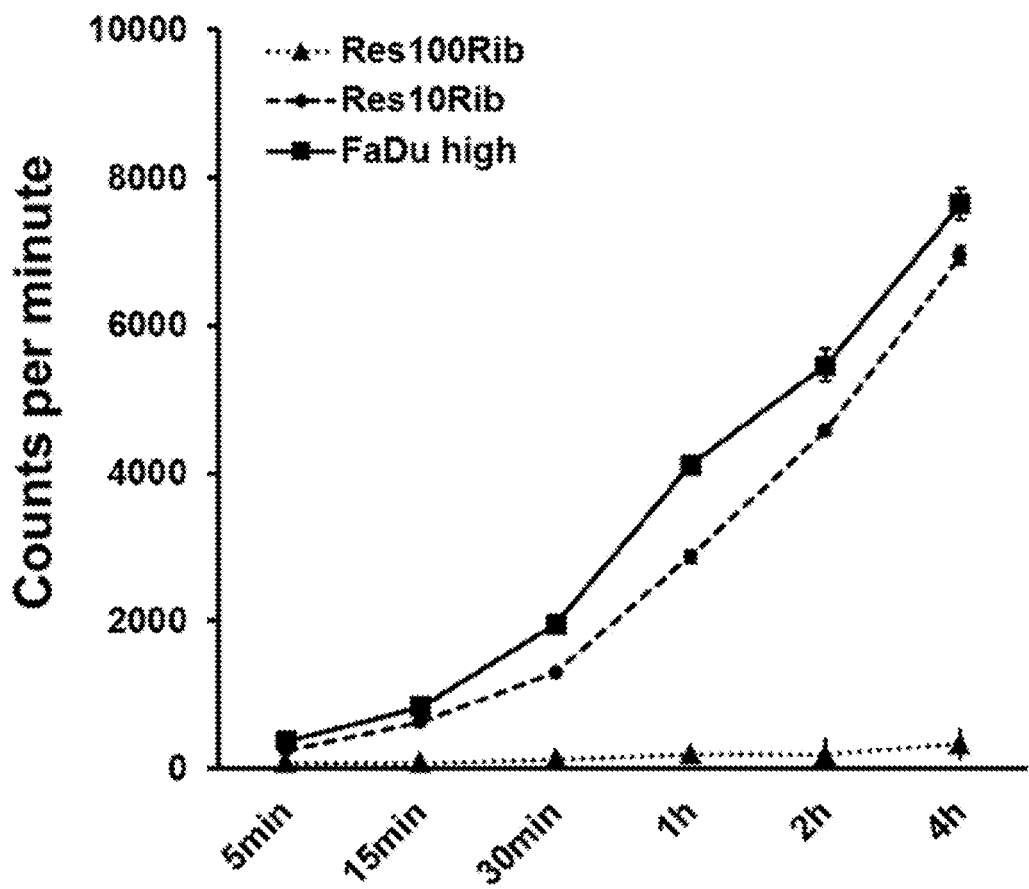
FIG. 5 is a graphical demonstration of the uptake of 3H-ribavirin as a potential mechanism for ribavirin resistance.

The uptake of $^{3}$H-ribavirin as a potential mechanism for ribavirin resistance was examined (FIG. 5). Previous studies indicate that maximal uptake is around 8-10 hours after ribavirin treatment. Uptake from 0 to 16 hours at different ribavirin concentrations was monitored. Parental FaDu and THP1 cells showed uptake profiles similar to those reported previously. The F100R, T10R and T20R cell lines all showed severe defects in ribavirin uptake. Interestingly, F10R cells, although resistance to ribavirin had uptake that was indistinguishable from parental FaDu cells. Thus, there are, at least, two major forms of ribavirin resistance, type I, which has a defect in net uptake, and type II which is characterized by normal uptake but loss of the interaction of ribavirin with eIF4E.

Ribavirin is taken up by all cells via the equilibrative nucleoside transporter ENT1 and once in the cell is phosphorylated to ribavirin monophosphate using adenosine kinase (ADK). Subsequent phosphorylation to its active metabolite, ribavirin triphosphate (RTP) occurs via a wide variety of cellular kinases. Real time quantitative PCR (RT-qPCR) methods and western blot analyses revealed that ADK and ENT1 were altered in the resistant THP cells but only ADK was altered in F100R cells. In F100R cells, ADK RNA levels are reduced 30 fold as assessed by RT-qPCR while ENT1 RNA levels are not changed. At the protein level, ADK protein levels are substantially reduced relative to parental cells indicating that ADK is reduced at the transcript level while ENT1 is downregulated post-transcriptionally. In THP1 cells, where ADK was downregulated at the transcript level whereas ENT1 is reduced post-transcriptionally in THP1 resistant cells, with the exception of T2×20R cells. T2×20R and F100R cells have normal protein and RNA levels of ENT1 (compared to parental cell lines) but do have very low levels of ADK RNA and protein. ADK defects alone are sufficient to reduce net uptake of ribavirin because the unphosphorylated ribavirin can be readily exported.

The Sonic Hedgehog Transcription Factor GLI1 Underlies Type II Resistance

F10R cells had no defect in ribavirin uptake and had normal levels of ADK and ENT1 RNA and proteins. Ribavirin did not associate with eIF4E in these cells, or target eIF4E activity. (FIG. 6) To determine the molecular underpinnings for this form of resistance, deep sequencing was used to compare F10R transcripts levels with those of F100R cells and with low and high passage parental FaDu cells.

Figure 7:
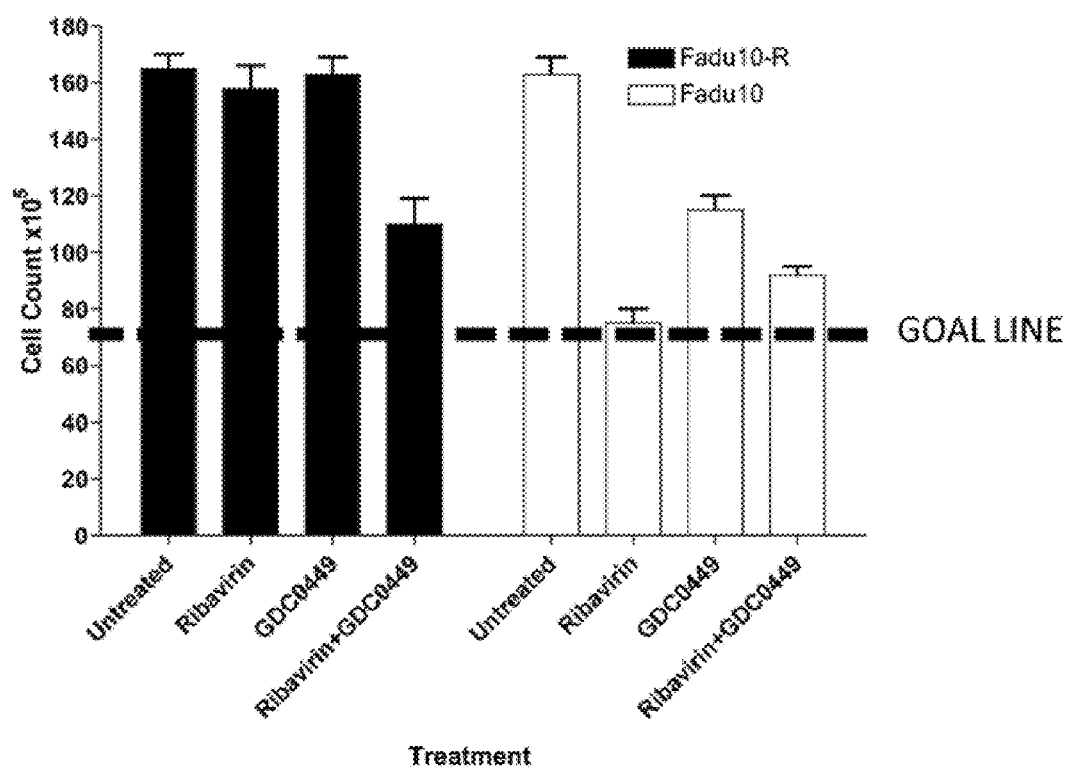
FIG. 7 is a diagram demonstrating Gli-1 hedgehog pathway inhibitor GDC-0449 (Roche) partially reverting ribavirin resistance. One treatment with 3 nM GDC-0449 followed 48 hours later with ribavirin.

Cross comparison of F10R versus all other groups indicated that less than 30 transcripts were different using a padj cutoff value of 0.01. (Table 1). The statistically most significant difference was glioma associated protein, Gli-1, which was elevated 20 fold in F10R cells versus the others. It was shown that Gli-1 was elevated at the RNA and protein levels in F10R cells using real time PCR and western analysis (FIG. 7). Elevation of Gli-1, the downstream transcription factor for signalling via the sonic hedgehog pathway, is associated with driving proliferation and resistance in other systems. The mechanism for the latter is usually attributed to the proliferative capacity of this signaling pathway.

TABLE 1

Gli-1 mRNA levels relative to multiple healthy volunteers

| Patient # | Response | Before | During response | Relapse/EOT |
|---|---|---|---|---|
| 17 | BR | 20 | 5.8 | 26 |
| 10 | BR | 1.3 | 1.6 | 3.6 |
| 6 | BR | 2.0 | n/a | 15 |
| 8 | PR | n/a | 0.1 | 2.0 |
| 11 | CR | n/a | 0.5 | 1.5 |
| 18 | SD | 6.4 | 2.7*20% drop in blasts | n/a |
| 13 | SD | 1.4 | 2.6* blasts elevated but still SD | 5.3 |
| 3 | SD | 7 | 12* blasts remained same | 23 |
| 9 | PD | 800 | — | n/a |
| 19 | PD | 19 | — | 36 |

Preliminary results from monotherapy trial for patients finishing one cycle.

Figure 6:
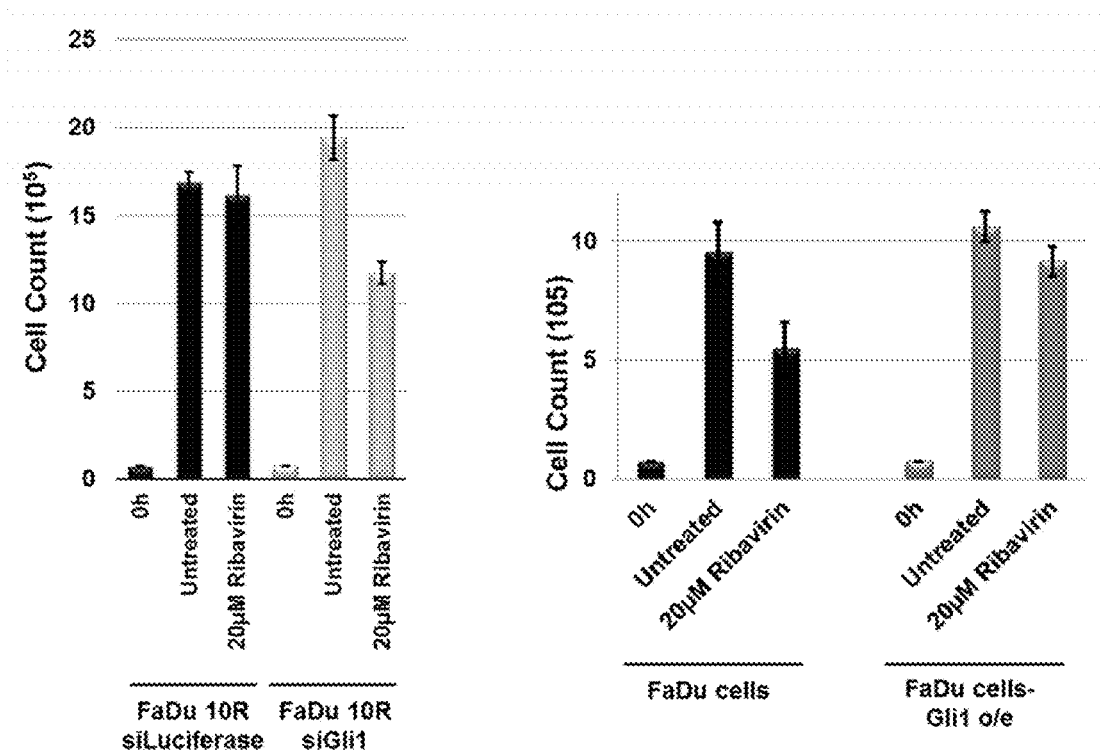
FIG. 6 is a diagram demonstrating knocking down Gli-1 reverts resistance and overexpressing Gli-1 imparts it. Aiming for 50% reduction for response as the experiment is done at the IC50 of this cell line.

It was examined whether Gli-1 overexpression alone was sufficient to impart resistance to ribavirin in FaDu cells. Gli-1 overexpressing cells were virtually unaffected by the addition of 20 µM ribavirin (95% of the untreated Gli-1 overexpressing cells) unlike the parental cells where treatment with 20 µM ribavirin reduced cell number by 50%. (FIG. 6). Gli-1 knockdown experiments were performed in parallel. Upon treatment with 20 µM ribavirin, growth of siRNA luciferase treated F10R cells was unaffected. In contrast, RNAi mediated knockdown of Gli-1 re-sensitizes F10R cells to ribavirin with cell numbers being about 50% of these same cells without ribavirin. siRNA medicated knockdown of Gli-1 alone had no effect on cell number for untreated F10R cells relative to control siRNAs indicating these effects were due to both treatments (siGli+ribavirin) and not effects of Gli-1 alone. Western blot analysis confirmed overexpression or knockdown of Gli-1. Further, eIF4E levels were not altered in these conditions.

A variety of sonic hedgehog pathway inhibitors have been developed and successfully used for targeting Smoothed, the extracellular receptor for sonic hedgehog signaling. One of these, GDC-0449, has been used in clinical trials for a variety of malignancies. To determine whether type II ribavirin resistance was sensitive to pharmacological intervention, the ability of GDC-0449 to revert resistance in F10R cells was assessed (FIG. 7.). Parental FaDu cells or F10R cells were pretreated with 3 nM GDC-0449 or mock treated and after 48 hours, were mock treated or treated with 10 µM ribavirin. In parental cells, 10 µM ribavirin for 96 hours led to a decrease in cell number by about 50% whereas 10 µM ribavirin did not effect growth of F10R cells relative to untreated F10R cells. Strikingly, the combination of ribavirin and GDC-0449 cells led to a 40% drop in cell number relative to the other treatments or untreated controls in F10R cells. Although this is not the full 50% drop observed in ribavirin treated parental cells, it clearly indicates that the addition of GDC-0449 to ribavirin resensitizes cells to ribavirin. This parallels the Gli-1 knockdown experiment described above. In contrast in parental cells, this combination did not reduce cell number below ribavirin only treated cells. Further, GDC-0449 alone led to a 25% reduction in growth in parental cells whereas GDC-0449 alone did not affect F10R cells. Finally, GDC-0449 had no effect on the growth of type 1 resistant F100R cells, which do not have elevated Gli-1. Taken together with above findings, these studies strongly suggest that type II ribavirin resistance can, at least in large part, be reverted by inhibition of the sonic hedgehog pathway. Further, the F10R cells have developed a co-dependency on Gli-1 and eIF4E pathways as observed by the need for both ribavirin and GDC-0449 to reduce growth. According to the present invention, Gli-1 knockdown did not affect the growth of F10R cells alone, but did in combination with ribavirin.

It was observed that the phase II drug metabolism pathway in the form of the UGT glucuronidation pathway was highly elevated in F10R cells, strongly suggesting that ribavirin is being glucuronidated in these cells as a novel form of resistance. The small molecule inhibitor of the sonic hedgehog pathway, GDC 0449 revert ribavirin resistance. Strengthening the tie between Gli-1 and resistance is the fact that genetic knockdown of Gli-1 also revert resistance and Gli-1 overexpression in ribavirin sensitive cells imparts resistance.

Gli-1 mRNA levels were monitored in patients before, during, and after response in patients receiving ribavirin monotherapy. To date, the non-responding patients before treatment had over 20 fold elevated ribavirin levels. These levels were not reduced during ribavirin treatment, indeed for one case that there is available data, the Gli-1 levels nearly doubled. For responding patients, in all cases Gli-1 mRNA levels were higher at resistance than during response. In some cases, ribavirin levels started high in the before treatment sample and then were reduced (for instance, patient 17 had 20× Gli-mRNA before treatment, 5.8 during blast response and 26× at relapse), whereas in other cases, Gli-1 mRNA levels started low and then became elevated at relapse (for instance, patient 10 had 1.3× Gli-1 mRNA before treatment relative to normal, 1.6× during response and 3.6× at relapse).

Ribavirin Resistance
Alterations in the Proteome and Gene Expression of Resistant Cell Lines as a Function of Ribavirin Treatment Deep sequencing in 10R cells during ribavirin treatment was carried out in order to monitor inducible changes and compare these to changes in parental cell lines. All deep sequencing in resistant cells is done in the absence of ribavirin. Addition of ribavirin did not alter the ENT1, ADK or Gli-1 levels.

Approved drugs were studied to ascertain modalities to overcome resistance, or the appearance of new sensitivities that occur upon the onset of resistance as observed for other drugs. It was also studied whether acquired resistance was reversible. After 6 months of growing resistant cells in the absence of ribavirin, these cells retained their resistance suggesting genetic changes underlie this.

The molecular underpinnings of primary and acquired resistance to ribavirin were assessed using two strategies:
  to generate resistant cell lines; and
  to analyze patient specimens for the expression of genes involved in ribavirin metabolism.

It has been noted that patients that only achieved PD in either trial, did not have a molecular response. Thus, the possibility that patients with no molecular response had issues with ribavirin uptake or metabolism was considered, or resistance arose due to elevated Gli-1.

The Applicant studied multiple ribavirin resistant cell lines. Resistant cell lines were generated by either slowly increasing ribavirin concentrations or by growing at constant ribavirin concentrations at clinically achievable doses. During the study, mutations in the eIF4E gene product were not observed in cell lines and are in the process of sequencing the eIF4E gene product in patient samples. Reduced/elevated the eIF4E gene product levels as a function of resistance in cell lines were not observed even after culturing in ribavirin for over 200 days. In all of studied resistant cell lines, a loss of ribavirin mediated growth inhibition was observed and a loss of response of eIF4E targets to ribavirin. Consistently, the eIF4E gene product can no longer immunoprecipitate $^3$H ribavirin in resistant cells in contrast to controls.

Both a candidate approach and deep sequencing were used to characterize ribavirin resistant cell lines. In two of the cell lines grown in 100 μM or 20 μM ribavirin (100R and 20R), cells had a severely impaired net uptake of $^3$H-ribavirin. Adenosine kinase (ADK) RNA levels were lowered 40-fold in 100R cells and both ADK and ENT1 were similarly reduced in 20R cells. ADK phosphorylates ribavirin to yield ribavirin monophosphate (RMP) as the first step to form its active metabolite RTP. Ribavirin is only exported via the ENT1 nucleoside transporter when it is not phosphorylated. Thus, reduction in ADK increases the pool of exportable ribavirin. The applicant noted that 10R cells showed no difference in ADK or ENT1 relative to parental cells nor did they have impaired ribavirin net uptake-3H ribavirin IP. Growth studies and monitoring the eIF4E gene product targets indicates that the 10R cells are resistant to the effects of ribavirin.

Figure 2:
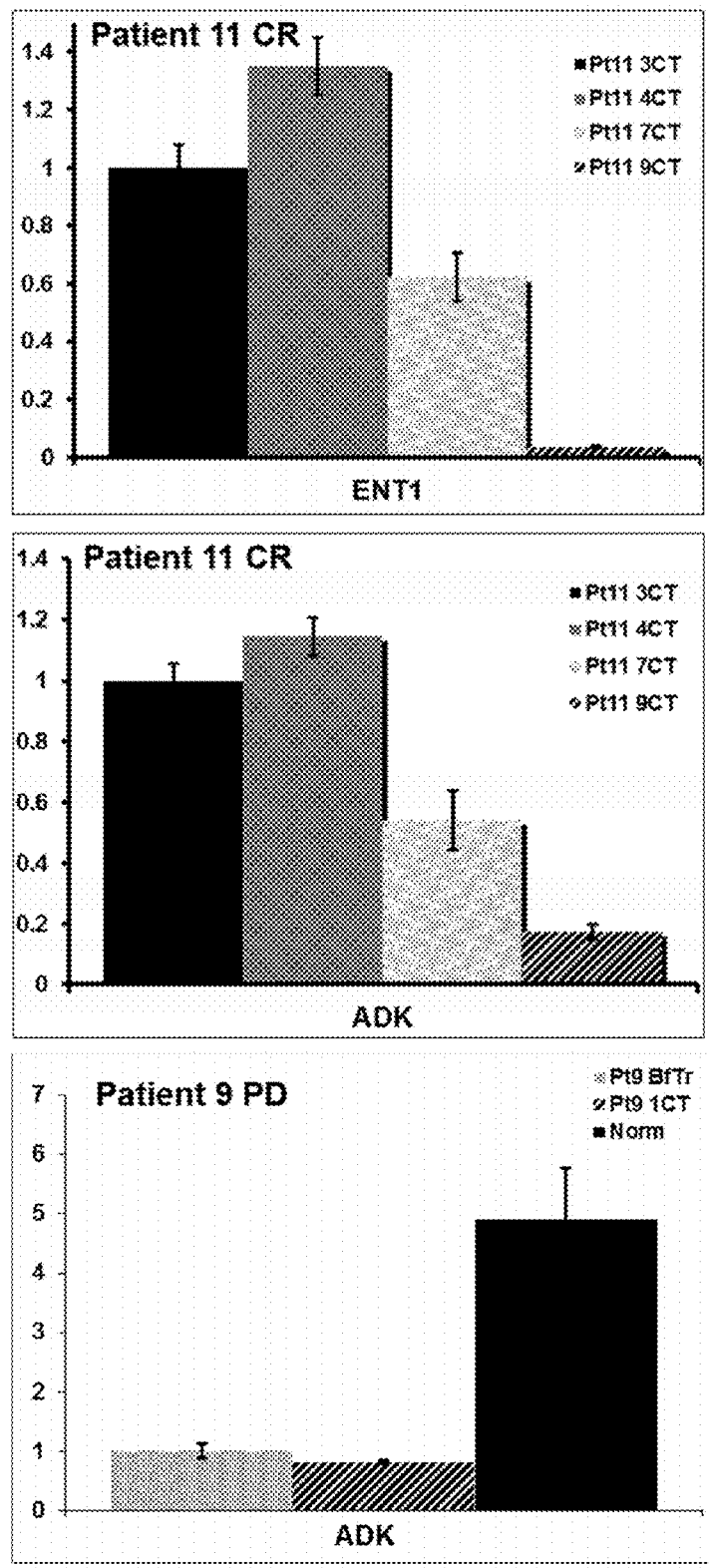
FIG. 2 is a diagram demonstrating ENT1 and ADK RNA levels as a function of ribavirin treatment in patients. CT is the number of 28 day cycles of ribavirin, normal is derived from normal CD34+ cells from the bone marrow. There was no more before treatment RNA available for patient 11, but he was responding at cycles 3 and 4 and clinical and molecular relapse occurred at cycle 9. For instance, in Patient 11 (CR), we observed a 20-fold reduction in ENT1 and a 5-fold reduction in ADK RNA levels at relapse relative to during response (after 9 cycles of treatment).
Figure 3:
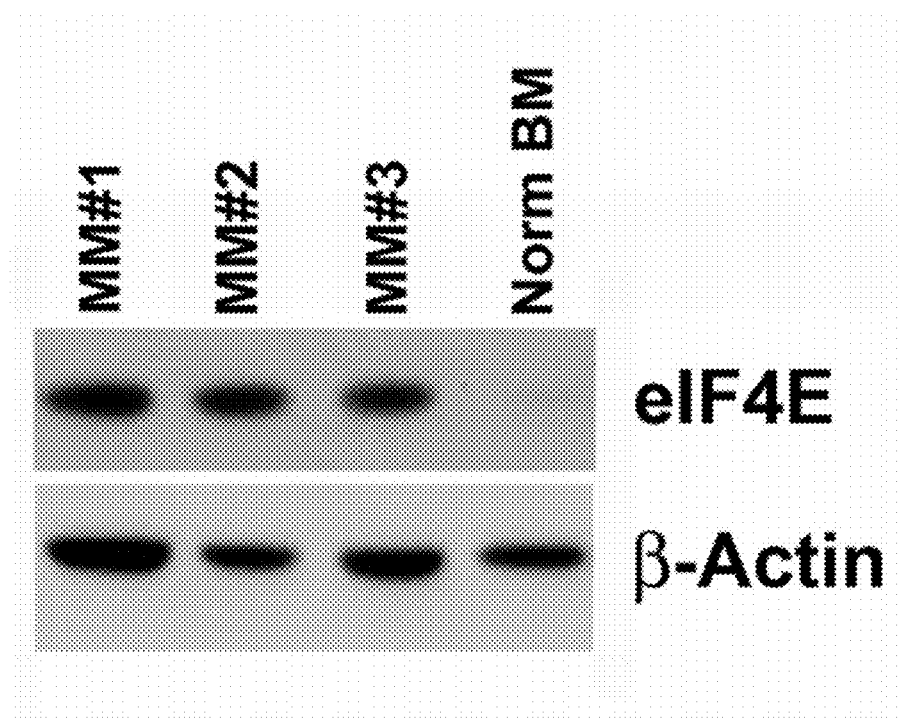
FIG. 3 is a western blot of three primary multiple myeloma specimens versus CD34+ cells isolated from normal bone marrow. It was determined that eIF4E levels are elevated in 3/3 multiple myeloma (MM) (FIG. 3), and 2/2 MDS specimens. Only 1/8 B-ALL specimens had elevated eIF4E. However, the one specimen that had elevated eIF4E contained a t4;11 translocation.

Gene expression changes using deep sequencing was assessed. Performed studies reveal a drastic increase in the RNA levels of Gli-1 (17×) and PDEA2 (22×) both of which have been linked to the establishment of resistance in F10R cells. Thus, F10R cells may have undergone substantial genetic rewiring and likely have lost their addiction to eIF4E. Applicant has noted in light of the studies performed that ribavirin resistance can arise due to multiple mechanisms. Whether these mechanisms were relevant or not in patients from the monotherapy trial was assessed. Patient 11 (CR), showed a 20-fold reduction in ENT1 and a 5-fold reduction in ADK RNA levels at relapse relative to during response (after 9 cycles of treatment) (See FIG. 2). Gli-1 levels changed (see table).

CT is the number of 28 day cycles of ribavirin, normal is derived from normal CD34+ cells from the bone marrow. Results from RT-qPCR are normalised against multiple genes to ensure no changes in the normalised occurred as described. There was no more before treatment RNA available for patient 11, but he was responding at cycles 3 and 4 and clinical and molecular relapse occurred at cycle 9.

In a PD, 5-fold lower ADK levels prior to therapy were observed compared to normal controls but had normal ENT1 levels. Patient 10 (BR, AML secondary to breast cancer) had a 3-fold reduction in ENT1 levels and concomitant 17-fold increase in MDR1 at relapse at four cycles. In other patients, none of these factors explained primary resistance or the onset of acquired resistance underlying the importance of studies in F10R cells and more patient specimen analysis. Clearly, in the heterogeneous background of these patients, resistance arises through multiple means.

There was no competition observed for the uptake of ribavirin and Ara-C® in patient specimens or cell lines. Both Ara-C® and ribavirin are taken up by nearly all cell types using the ENT1 transporter and the oral absorption issues have been identified in phase I trial and have examined ribavirin and Ara-C® uptake. Using ribavirin and $^3$H-Ara-C®, no competition in terms of uptake for either drug was observed at clinically relevant concentrations (and higher) in patient specimens or cell lines.

Glucuronidation Enzymes are Elevated in Type II Resistant Cells

Figure 8:
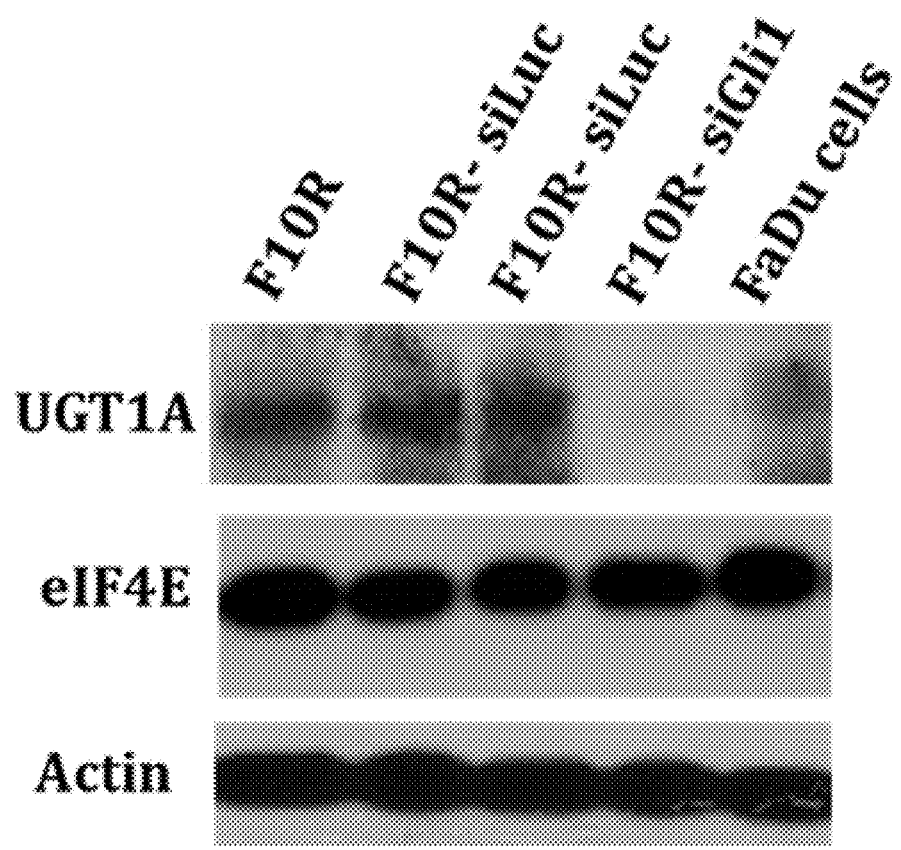
FIG. 8 is a Western analysis of glucuronidation pathway enzymes (UGT1As) which are elevated in F10R resistant cells with normal uptake relative to parental cell lines or other resistant ones.

A deep sequencing study also revealed a striking change in the enzymes in the glucuronidation pathway in F10R cells. The UDP glucuronosyltransferase type 1A (UGT1A) family of enzymes plays key roles in phase II detoxification and drug metabolism. Although these activities were initially considered limited to the liver, most cell types are now known to have UGT activity. Surprisingly, there was the 14 fold depletion in the RNA levels of nearly all the UGT1A family of enzymes including A1, A3, A4, A5, A6, A7, A8, A9 and A10 (padj values from 5×10−8 to 1×10−9). This depletion was confirmed by qRT-PCR in F10R cells. Note that UGT1A2 RNA was not detected in any of the cell lines examined, including parental cells. Importantly, there was no change observed in the UGT2 class of these enzymes. The UGT1A enzymes are transcribed from a common gene locus through an exon sharing mechanism and thus have a common carboxy terminus, and all have approximately the same molecular weight. Thus, an antibody that recognizes the UGT1A family was used to assess protein levels (FIG. 8). In direct contrast to the RNA levels, protein levels of the UGT1A family were highly elevated (3-4 fold) in F10R cells relative to parental cell lines or F100Rs. This is evidence of a complex regulatory mechanism governing the UGT pathway in F10R cells.

Whether there was a link between Gli-1 elevation and increased protein expression of UGT was examined. Parental FaDu cells overexpressing GLi-1 had higher UGT levels relative to vector controls. RNAi mediated knockdown of Gli-1 led to substantial reduction (over 10 fold) in UGT1A protein levels compared to the knockdown of luciferase RNA and untreated controls. Consistent with these findings, GDC-0449 treatment led to a similar decrease in UGT1A levels. Taken together, these results provide a strong link between Gli-1 levels, and protein expression of UGT. Controls confirmed that Gli-1 overexpression or reduction in knockdown cells. Further, none of these treatments modulated eIF4E levels. UGT1A protein expression strongly correlates with its enzyme activity. Thus, it was hypothesized that glucuronidation activity, at least for some substrates, was elevated in F10R cells relative to parental controls.

Glucuronidation of Ribavirin is Elevated in Resistant Cells and Impairs Interaction with eIF4E The UGT1A family catalyzes the addition of UDP-glucuronic acid (UDPGA) to a myriad of substrates including triazoles, the same chemical class as ribavirin. Importantly, different UGT enzymes have different target specificities and thus substrates can be glucuronidated in a tissue and cell type in a specific manner. Whether there was differential glucuronidation of ribavirin in FaDu cells versus F10R cells was monitored. Using cell/microsomal lysates, $^{14}$C-UDPGA and ribavirin glucoronidation was monitored using thin layer chromatography. The converse experiment with unlabelled UDPGA and $^{14}$C-ribavirin was also carried out. As a positive control, the glucuronidation of benzo(a)pyrene, a common target of this pathway that is one of the main carcinogens in cigarette smoke was monitored.

It was hypothesized that glucuronidation of ribavirin impairs its association with eIF4E. The ability of eIF4E to immunopreciptate with $^{14}$C-ribavirin in conditions that varied in Gli-1 and UGT activity was monitored to determine if reversion of resistance correlated with re-association of ribavirin with eIF4E. Cells were treated for 24 hours with $^{14}$C-ribavirin followed by cross-linking and immunoprecipitation and evaluated relative to IgG controls. This demonstrated that in F10R cells, eIF4E did not immunoprecipitate with ribavirin whereas it did in parental cells.

GDC-0449 treatment or Gli-1 knockdown in F10R cells led to an increase in ribavirin binding to eIF4E, which correlated with lowering of UGT levels. In parental cells overexpressing Gli-1, there was a loss in association of ribavirin to eIF4E. This indicates a correlation between lower Gli-1 activity, lower UGT levels, and the ability of eIF4E to associate with unmodified ribavirin and resistance.

Gli-1 Elevation in Clinical Samples from the AML Ribavirin Monotherapy Trial

The molecular features identified in present studies were examined to determine whether they were relevant to specimens from patients that received ribavirin monotherapy in the multi-centre phase II AML trial. For responding patients, all available specimens before treatment were monitored, during clinical response, upon the onset of relapse and in non-responders when possible. A total of ten specimens were examined including those from patients that enrolled in the monotherapy trial. Results from the trial, when closed, were 1 CR, 2 PR, 3 BR, 6 SD, 3 PD with 15 evaluable patients (Clinicaltrials.gov). Of these, samples from 10 patients were available for evaluation of molecular response. The results from the testing carried out suggest that type II resistance is observed in many of these patients. Gli-1 mRNA levels were monitored using qRT-PCR. Of the 6 responding patients who had specimens at relapse, all showed elevated Gli-1 mRNA levels, up to 26 fold, upon resistance relative to normal controls or their levels during response. Some patients have elevated Gli-1 prior to ribavirin monotherapy, which falls during response and reemerges at loss of response. For the two patients examined that did not respond (PD), both had highly elevated Gli-1 levels prior to treatment (19 and 800 fold), which was not lowered after 28 days of ribavirin. Taken together, it appears that elevated Gli-1 is associated with primary and acquired resistance in patients in the ribavirin monotherapy trial. (See above table).

In terms of type I resistance, one non-responder (patient 9) was observed to have five times lower ADK levels than specimens from healthy volunteers prior to treatment. In the patient that achieved a CR (patient 11), it was observed that during response ENT1 and ADK RNA levels fell 15 and 5 fold, respectively, upon relapse relative to response. Thus, there is evidence that type I resistance plays a role in patients. However, the remaining patients did not have lower ADK RNA levels or marked alterations in ENT (at the RNA level). These findings suggest that type I resistance can also contribute to primary and acquired resistance in at least some patients. Further, patient 11 had both lower ADK levels and highly elevated Gli-1 levels, suggesting that these forms of resistance can co-emerge.

In contrast to type I resistance, type II is characterized by no defect in ribavirin uptake but a loss of the eIF4E-ribavirin interaction correlating with the elevation of Gli-1 mRNA and protein levels. Strikingly, overexpression of Gli-1 alone was sufficient to make parental cells resistant to ribavirin and was sufficient to abrogate the eIF4E-ribavirin interaction. In contrast, pharmacological inhibition using GDC-0449 or genetic knockdown of Gli-1 revert ribavirin resistance in the F10R cells and this correlates with a re-establishment of the eIF4E-ribavirin interaction. Importantly, primary and acquired resistance in the ten patient specimens examined indicated that Gli-1 levels were high prior to therapy and/or became elevated at the onset of resistance suggesting that targeting Gli-1 with GDC-0449, or related drugs, in patients could help overcome primary resistance and perhaps, prolong clinical responses.

Studies with chemical carcinogens link lowered UGT1A levels with increased carcinogenesis because of the loss of this important detoxification pathway. Gilbert's and Crigler-Najjar' syndromes, genetic diseases characterized by mutation of UGT1A1, lead to decreased glucuronidation of bilirubin, and varying severity in associated toxicity. The inventors of the present invention have determined that increased UGT1A activity shows a correlation to drug resistance. In this way, the cancer cell can subvert normal detoxification processes in order to modify the drug and become resistant. The inventors of the present invention have identified a drug, GDC-0449, that can modulate glucuronidation, albeit indirectly.

Drug resistance is usually considered to occur by one of two mechanisms. First, as observed in type I resistance, there is either a loss or mutation of relevant drug transporters or in the enzymes that convert pro-drugs to their active forms. Alternatively there is mutation/modification of the protein target/pathway. However, mutation in the eIF4E gene in studied cell lines was not observed. In contrast, Gleevec® or ATRA treatment can lead to mutations in Bcr-Abl and PML-RARA fusion proteins, respectively, which drive resistance. While neither Bcr-Abl nor PML-RARA are required for survival of normal cells, eIF4E is essential where in yeast, its knockout is lethal. Thus, stochastic mechanisms that drive resistance via mutation in the cap-binding site of eIF4E likely end with slow growing or dying cell populations and thus, are easily competed out by other forms of resistant cells. In this way, resistant mechanisms targeting proteins that are required for cellular survival may be distinct from those targeting proteins that are dispensable for normal cellular function. In these situations, resistance can be driven by chemical modification of the drug rather than only by mutation or modification of the target protein.

Deep sequencing reveals that cells have also become more malignant in the face of ribavirin resistance, with levels of eIF4E targets such as VEGF becoming elevated even upon ribavirin treatment.

The invention claimed is:

1. A method or the treatment of leukemia in a host in need thereof comprising administering ribavirin and GDC-0449.

2. The method according to claim 1, further comprising administering an additional chemotherapeutic agent, wherein the chemotherapeutic agent is cytarabine.

3. The method according to claim 2, wherein the cytarabine is administered in a low dose ranging from about 5 μM to about 15 μM per day.

4. The method according to claim 3, wherein the low dose of cytarabine ranges from about 10 mg per day to about 20 mg twice a day.

5. The method according to claim 3, wherein the cytarabine is administered in an amount up to 100 $mg/m^2$ per day, for up to 7 days every 4 weeks.

6. The method according to claim 2, wherein the GDC-0449 is co-administered sequentially or simultaneously with the ribavirin prior to administration of the cytarabine.

7. The method according to claim 6, wherein the ribavirin and GDC-0449 are administered in a single unit dosage form.

8. The method according to claim 7, wherein said composition is suitable for inhalation, ocular administration, nasal instillation, parenteral administration, dermal administration, transdermal administration, buccal administration, rectal administration, sublingual administration, perilingual administration, nasal administration, topical administration or oral administration.

9. The method according to claim 6, wherein the GDC-0449 is administered in an amount of about 3 µM for two days prior to start of administration of the ribavirin.

10. The method according to claim 6, comprising the steps of administering a therapeutically effective amount of GDC-0449 in the presence of a therapeutically effective amount of ribavirin, wherein such step of administering minimizes resistance previously developed in patients during anti-neoplastic treatment by reduction of UGT1A protein levels and inhibition of Gli-1 overexpression.

11. The method according to claim 2, wherein the GDC-0449 and the cytarabine are simultaneously or sequentially co-administered.

12. The method according to claim 11, wherein GDC-0449 and cytarabine are administered in a single unit dosage form.

13. The method according to claim 2, wherein the ribavirin and the GDC-0449 are administrated simultaneously or sequentially with the cytarabine.

14. The method according to claim 13, wherein the method comprises administering a pharmaceutical composition comprising ribavirin, GDC-0449, and cytarabine.

15. The method according to claim 1, wherein the ribavirin is administered in an amount between about 1000 and about 4400 mg per day.

16. The method according to claim 15, wherein the plasma levels of ribavirin range from about 4 to about 10 µM, as determined by mass spectrometry.

17. The method of combination therapy according to claim 15, wherein the plasma levels of ribavirin are above 20 µM, as determined by mass spectrometry.

18. The method according to claim 15, wherein the ribavirin is administer to a patient at levels sufficient to effect the eIF4E gene product re-localization and to achieve a durable complete molecular response.

19. The method according to claim 18, wherein said complete molecular response is selected from the group consisting of: complete remission (CR), partial remission (PR), blast response (BR), and stable disease (SD) but not progressive disease (PD).

20. The method according to claim 1, wherein the leukemia is selected from the group consisting of: acute myeloid leukemia, acute myelocytic leukemia, acute myeloblastic leukemia, acute lymphoblastic leukemia, acute promyelocytic leukemia, acute myelomonocytic leukemia, acute monocytic leukemia, acute erythroleukemia, chronic leukemia, chronic myelocytic leukemia, chronic myelogenous leukemia, chronic lymphocytic leukemia, and myelodysplastic syndromes.

21. The method according to claim 20, wherein the acute myeloid leukemia is selected from the group consisting of: acute myeloid leukemia M4, acute myeloid leukemia M5 and AML subtypes characterized by atypical elevation of the eIF4E gene product.

22. A method for treating patients having resistance to therapy, to overcome resistance previously developed during anti-neoplastic treatment or to overcome primary resistance or resistance due to prior therapy, wherein the method comprises administering ribavirin, GDC-0449 and cytarabine.

23. The method according to claim 22, wherein said method overcomes resistance previously developed in patients during anti-neoplastic treatment by inhibiting the expression of a gene in a patient.

24. The method according to claim 23, wherein said gene is selected from the group consisting of: Gli-1, Gli-2, Gli-3, Patched Ptch, Sonic hedgehog (Shh), signalling pathway, and a combination thereof.

25. The method of treatment according to claim 1 wherein the method comprises administering a therapeutically effective amount of ribavirin and a therapeutically effective amount of GDC-0449, and wherein the ribavirin and GDC-0449 are administered simultaneously or sequentially in resistant cell lines.

26. A method of treating leukemia to reduce eIF4E level and re-localize the eIF4E gene product in the patient, wherein the method comprises administration of ribavirin with GDC-0449.

* * * * *

UNITED STATES PATENT AND TRADEMARK OFFICE
CERTIFICATE OF CORRECTION

| | | |
|---|---|---|
| PATENT NO. | : 9,545,416 B2 | Page 1 of 1 |
| APPLICATION NO. | : 14/344536 | |
| DATED | : January 17, 2017 | |
| INVENTOR(S) | : Borden et al. | |

It is certified that error appears in the above-identified patent and that said Letters Patent is hereby corrected as shown below:

In the Specification

In Column 1, Line 54, delete the word "or" and insert the word --for-- therefor.

In the Claims

In Column 31, Line 46, delete the word "administer" and insert the word --administered-- therefor.

Signed and Sealed this
Twenty-third Day of May, 2017

Michelle K. Lee
*Director of the United States Patent and Trademark Office*

UNITED STATES PATENT AND TRADEMARK OFFICE
CERTIFICATE OF CORRECTION

PATENT NO. : 9,545,416 B2
APPLICATION NO. : 14/344536
DATED : January 17, 2017
INVENTOR(S) : Katherine Borden et al.

Page 1 of 1

It is certified that error appears in the above-identified patent and that said Letters Patent is hereby corrected as shown below:

In the Claims

Column 30, Line 54, Claim 1 delete the word "or" and insert the word -- for -- therefor.

Column 31, Line 46, Claim 18 delete the word "administer" and insert the word -- administered -- therefor.

This certificate supersedes the Certificate of Correction issued May 23, 2017.

Signed and Sealed this
Twenty-first Day of April, 2020

Andrei Iancu
*Director of the United States Patent and Trademark Office*